US006281250B1

(12) United States Patent
Shealy

(10) Patent No.: US 6,281,250 B1
(45) Date of Patent: Aug. 28, 2001

(54) RETINYL ETHERS, DERIVATIVES AND ANALOGUES AND INHIBITION OF BREAST CARCINOGENESIS

(75) Inventor: Y. Fulmer Shealy, Birmingham, AL (US)

(73) Assignee: Southern Research Institute, Birmingham, AL (US)

( * ) Notice: Subject to any disclaimer, the term of this patent is extended or adjusted under 35 U.S.C. 154(b) by 0 days.

(21) Appl. No.: 09/289,748

(22) Filed: Apr. 12, 1999

Related U.S. Application Data

(60) Provisional application No. 60/081,482, filed on Apr. 13, 1998.

(51) Int. Cl.[7] ............... A61K 31/075; A61K 31/085; A61K 31/12; C07C 43/205; C07C 49/747
(52) U.S. Cl. ............... 514/683; 514/717; 514/719; 568/329; 568/631; 568/640; 568/646; 568/659; 568/660; 568/661
(58) Field of Search ............... 568/329, 631, 568/646, 640, 659, 660, 661; 514/683, 717

(56) References Cited

U.S. PATENT DOCUMENTS 5,610,200  3/1997  Hammerling et al. ............... 514/763

OTHER PUBLICATIONS

Sani, B.P., "Retinoids New Trend in Research and Clinical Applications," Oct., 21–24, 1991.
Negishi et al., Chemical Abstracts, vol. 116, abstract 83955, 1992.*
Naarmann et al., Chemical Abstracts, vol. 110, abstract 213689, 1989.*
Jaeger et al., Chemical Abstracts, vol. 119, abstract 130925, 1993.*
Shealy, Y.F. et al. (1998). "Retinyl substituted–benzyl ethers. Inhibition of mammary carcinognesis by retinyl 3,4,5–trimethoxybenzyl ether (RTMBE)," *Anti–Cancer Drug Des.* 13:159–182.
Jaeger, E.P. et al. (1993). "Structure–activity relationship studies of retinoid cancer inhibition," *Eur. J. Med. Chem.* 28:275–290.
Shealy, Y.F. et al. (1997). "Retinyl ethers as cancer chemopreventive agents. Suppression of mammary cancer," *Anti–Cancer Drug Des.* 12:15–33.
Kaleagasioglu, F. et al. (1993). "Antiproliferative Activity of Retinoic Acid and Some Noel retinoid Derivatives in Breast and Colorectal Cancer Cell Lines of Human Origin," *Arzneimittel Forschung. Drug Res.* 43:487–490.
Tetzner et al., *Chemical Abstracts*, Mutation Research, 79(1980) 163–167.
Shealy et al., *Chemical Abstracts*, vol. 130(1997) 75643.
Nuerrenbach et al., *Chemical Abstracts*, vol. 88(1977) 121450.

* cited by examiner

*Primary Examiner*—Richard L. Raymond
(74) *Attorney, Agent, or Firm*—Rothwell, Figg, Ernst & Manbeck, P.C.

(57) ABSTRACT

The present invention is directed to retinyl ethers, derivatives and analogues and their use in inhibiting breast carcinogenesis or breast cancer cell growth.

16 Claims, 1 Drawing Sheet

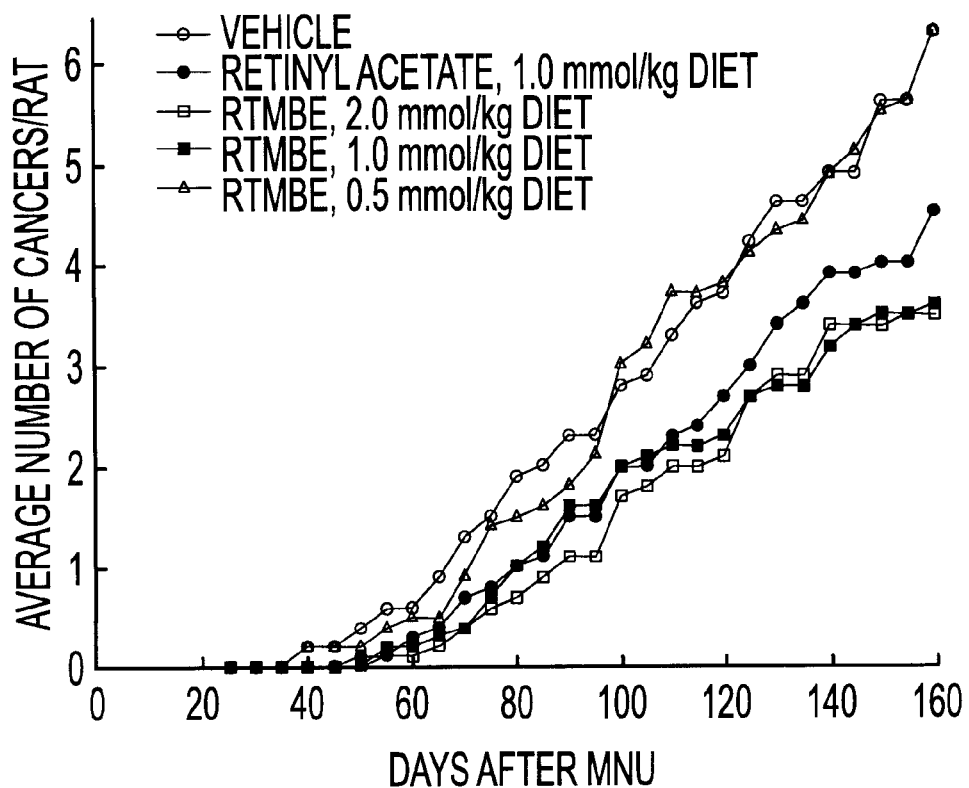
FIGURE

RETINYL ETHERS, DERIVATIVES AND ANALOGUES AND INHIBITION OF BREAST CARCINOGENESIS

CROSS REFERENCE TO RELATED APPLICATION

The present application is related to U.S. provisional patent application Ser. No. 60/081,482, filed Apr. 13, 1998, incorporated herein by reference.

This invention was made with Government support under Grant No. P01-CA34968, awarded by the National Institutes of Health, Bethesda, Md. The United States Government has certain rights in the invention.

BACKGROUND OF THE INVENTION

The present invention is directed to retinyl ethers and derivatives and their use in inhibiting breast carcinogenesis or breast cancer cell growth.

The publications and other materials used herein to illuminate the background of the invention, and in particular, cases to provide additional details respecting the practice, are incorporated herein by reference, and for convenience, are referenced by author and date in the following text and respectively grouped in the appended List of References. All patents and published patent applications are incorporated herein by reference.

It is well established that retinoids are prime candidates for the prevention of some forms of cancer. Numerous studies in experimental models of cancer in animals have demonstrated that certain retinoids suppress or delay the development of carcinogen-induced malignancies (Sporn, 1977; Sporn, 1980; Hill and Gribbs, 1982; Sporn and Roberts, 1984, Hill and Grubbs, 1992; Moon et al., 1994). Initially, some of the natural retinoids, e.g., retinol (or retinyl esters), retinoic acid (or retinoates), retinal, 13-cis-retinoic acid, were found to exert cancer chemopreventative effects in vivo (Sporn, 1977; Hill and Grubbs, 1982; Sporn and Roberts, 1984; Moon and Itri, 1984; Sporn et al., 1976). However, the usefulness of natural retinoids for cancer chemoprevention is limited because of their toxicity in pharmacological doses, storage of retinyl esters in the liver and the resulting hepatotoxicity, inadequate target-organ specificity and insufficient accumulation in target organs (Sporn, 1977; Sporn, 1980; Sporn et al., 1976). This has led to the study of retinoid derivatives for use as chemopreventative agents.

There are many reports, which have been summarized previously (Lotan et al., 1980; Shealy, 1989) that retinyl methyl ether (RME) is active in various bioassays in vitro. In addition, RME has been shown to suppress 7,12-DMBA-induced (Grubbs el al, 1977) and MNU-induced (Thompson et al., 1978) mammary cancer in rats. However, as pointed out previously (Shealy, 1989; Shealy et al., 1997) reports of the demethylation of RME by microsomal oxidases to retinol (Thompson and Pitt, 1963; Narindrasorasak et al., 1971; Narindrasorasak and Laksmanan, 1972) apparently discouraged further investigations of RME and other retinyl ethers. Nevertheless, the rationale for reviving investigations of retinyl ethers was outlined (Shealy, 1989) and became the basis for the synthesis of new retinyl ethers, especially, for evaluation against carcinogen-induced mammary cancer. It was postulated that some new retinyl ethers -unlike RME -might not be converted to retinol, but might accumulate in mammary tissue.

Two of the new retinyl ethers, retinyl propynyl ether (RPE) and retinyl 3-methyl-2-butenyl ether (RMBE), inhibited the development of MNU-induced mammary cancer (Shealy et al., 1997). During these studies, it was shown that RPE accumulated in rat mammary tissue and that RPE and RMBE did not cause (because of the low- or non-conversion of these derivatives to retinol) accumulation of large amounts of retinyl palmitate in the liver, a toxic effect produced by efficacious amounts of retinyl acetate or RME. RMBE was only modestly active in the 90-day anti-carcinogenesis study. RPE appeared to be more effective than retinyl acetate (the positive control retinoid), but it slowly undergoes an intramolecular Diels-Alder reaction in the solid state and in solution (Shealy et al., 1996, 1997), and also causes some increase in retinyl palmitate in the liver.

Thus, it is desired to identify additional retinyl ether derivatives which have chemopreventative activity and can be used to inhibit carcinogenesis, especially breast carcinogenesis, or to inhibit breast cancer cell growth, and which do not have disadvantages of prior retinyl ethers.

SUMMARY OF THE INVENTION

The present invention is directed to retinyl ethers and derivatives and their use in inhibiting breast carcinogenesis or breast cancer cell growth.

In one aspect, the present invention is directed to retinyl ethers and derivatives having the general formula $$X\text{—}O\text{—}(CRR^1)_n\text{—}Y \qquad (I)$$

wherein R and $R^1$ are independently H, F, Cl, $C_1$–$C_{10}$-alkyl, $C_1$–$C_{10}$-alkyl halide, $C_1$–$C_{10}$-alkoxy, phenoxy or an aryl group; n is 0 or 1; Y is an unsubstituted or substituted aryl or an unsubstituted or substituted heterocyclic ring structure having 1 to 4 heteroatoms; and X has one of the following structures

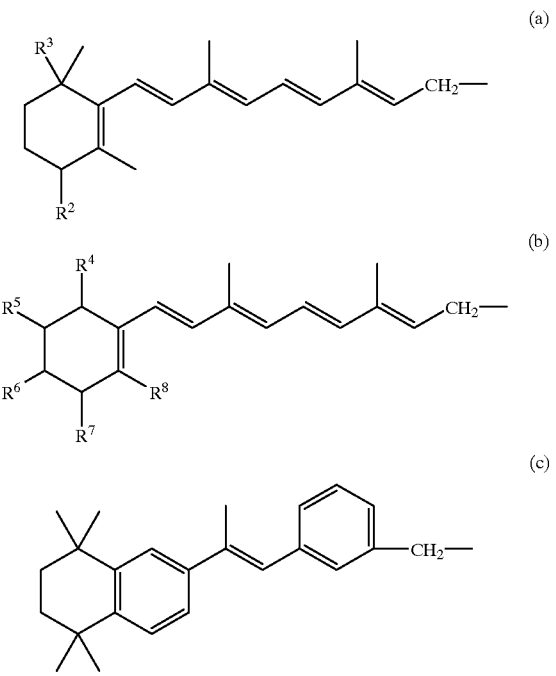

-continued

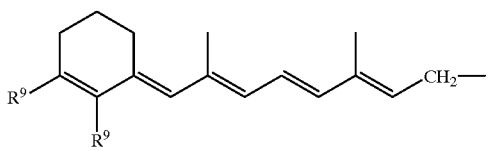

(e)

wherein $R^2$ is H, OH or =O, $R^3$ is $CH_3$ or $CH_2OH$, $R^4$, $R^5$, $R^6$, $R^7$ and $R^8$ are independently H, OH, halogen, COOH, $CH_2OH$, $C_1$–$C_{10}$-alkyl, $C_1$–$C_{10}$-alkyl halide, $C_1$–$C_{10}$-alkoxy, phenoxy or an aryl group, and $R^9$ is H, or $C_1$–$C_5$ alkyl. The heterocyclic ring may contain a single ring structure or may contain a fused ring structure. Examples of substituents for Y are H, OH, halogen, $C_1$–$C_{10}$-alkyl, $C_1$–$C_{10}$-alkyl halide, $C_1$–$C_{10}$-alkoxy, phenoxy or an aryl group, and 1 to 5 substituents may be present. Examples of aryl groups include, but are not limited to, phenyl, naphthyl, indenyl, anthracenyl or phenanthrenyl. Examples of heterocyclic rings include, but are not limited to, pyridine, indole, pyrimidine, purine, pyrazine, thiophene, furan, pyrrole, imidazole, oxazole, thiazole, pyrazole, quinoline, isoquinoline, pyrrolidine or 3-pyrroline. The novel compounds of the present invention include the compounds of Formula I, with the proviso that when R and $R^1$ are both H, X is structure (a), $R^2$ is H, $R^3$ is $CH_3$, and n is 1, then Y is not trimethoxyphenyl.

In a second aspect, the present invention is directed to a method for inhibiting breast cancer and/or breast cancer cell growth by administering an effective inhibitory amount of a compound of Formula I, optionally in combination with other anti-cancer agents.

In a third aspect, the present invention is directed to pharmaceutical compositions containing one or more of the compounds of Formula I, optionally also containing other anti-cancer agents.

BRIEF DESCRIPTION OF THE FIGURE

The FIGURE shows the effect of all-trans-retinyl 3,4,5-trimethoxybenzyl ether (RTMBE) on the number of mammary cancers induced in female Sprague-Dawley rats by N-methyl-N-nitrosourea (MNU) during a 160-day study. RTMBE was incorporated in the feed at doses of 2 mmole (934 mg) per kg, 1 mmole (467 mg) per kg, or 0.5 mmole (234 mg) per kg. Retinyl acetate was administered in the same way at 1 mmole (328 mg) per kg.

DETAILED DESCRIPTION OF THE INVENTION

The present invention is directed to retinyl ethers, derivatives and analogues and their use in inhibiting breast carcinogenesis or breast cancer cell growth.

In one aspect, the present invention provides retinyl ethers, derivatives and analogues having the general formula $$X—O—(CRR^1)_n—Y \qquad (I)$$

as described above. The synthesis of these compounds is described with reference to the retinyl benzyl ethers. Other ethers are prepared analogously using the appropriate starting materials. Derivatives and analogues of the retinyl moiety of the compounds are prepared by enzymatic oxidation of the retinyl moiety or by chemical modification as known in the art. Exemplary of such methods inlcude Modani et al. (1986), Loeliger et al. (1980), Mayer et al. (1978), Rosenberg et al. (1982), Blaner and Olson (1994), Aig et al. (1987), Nagai et al. (1994) and Vaezi et al. (1994).

The retinyl benzyl ethers (such as 2 and 3, structures shown in Table 1) are prepared by adding a DMF solution of a benzyl bromide or chloride to a solution of lithium retinoxide in benzene or a solution of sodium retinoxide in DMF. The retinoxide solutions are prepared, respectively, from n-butyllithium or sodium hydride and retinol. Retinol is obtained by hydrolyzing specimens of commercial retinyl acetate, most of which contained small amounts (2–4%) of 13-cis-retinyl acetate. Although retinol is obtained in a high state of purity (>99%) by crystallization, the crude product is frequently used for the preparation of 2 and 3, especially when large quantities of the ethers are required for evaluations in vivo. As outlined in the the Examples, the crude retinyl benzyl ethers are purified by the employment of successive chromatographic procedures. Subsequently, an improved procedure for the preparation of RTMBE furnished the purified product from a single flash-chromatographic operation.

After RTMBE had been shown in an initial study to suppress mammary cancer in vivo and to bind to CRBP, the retinyl benzyl ether structure was modified in the benzyl moiety according to the following pattern: the introduction of two methoxy groups (3a–b) at two of the positions occupied by the three methoxy groups of RTMBE; the preparation of the 2,5-dimethyl analogue (3c) because the corresponding dimethoxy derivative (3b) proved to be a good binder to CRBP (Table 2); the elimination of substituents (3d) to determine how the absence of substituents would affect binding to CRBP; the introduction of substituents again in the form of monomethoxy analogues (3e–f), a monomethyl analogue (3g), and another dimethoxy analogue (3h) because the unsubstituted analogue (3d) does not bind significantly to CRBP; the return to trisubstituted derivatives represented by the 2,3,4-trimethoxy analogue (3i) of RTMBE and the 2,4,6-trimethyl analogue (3j); the introduction of chloro substituents (3k–l); and the synthesis of an α-substituted analogue (3m). Other modifications include (a) ethers containing heterocyclic rings or (b) modifications of the retinyl moiety as shown in Formula I.

During the preparation of some of the retinyl benzyl ethers, the formation of a by-product that appeared to be anhydroretinol (4) was observed by TLC or HPLC, as seen during the preparation of other retinyl ethers (Shealy, et al., 1997). When a retinyl benzyl ether, such as 3b, is treated with a weakly acidic ethanol solution, 4 is isolated, as seen for retinol (Shantz et al, 1943, Shealy el al., 1996). Retinyl ethers must be rigorously protected from air, light, and acids; however, under these precautionary conditions, purified retinyl ethers are stable. As reported previously (Shealy et al, 1997), only minor degradation of RME occurred in refluxing ethanol (protected from light and air) during 24 hours, and under similar conditions, intramolecular cyclization of RPE and the 2-butynyl ether (1e) predominate with little, or no, formation of 4. Re-analysis of a specimen of RTMBE that had been stored during 5 years at −20° C. in an inert atmosphere showed that it was unchanged (V, HPLC (99.2%), $^1$H NMR). In addition, HPLC analyses of rigorously protected solutions of RTMBE in absolute ethanol or DMSO, solvents frequently used in preparing solutions for bioassays, showed that RTMBE was practically unchanged at 25.5±1.5° C. after 7 days in ethanol and changed very little during the same period in DMSO. Furthermore, RPE, RTMBE, and other retinyl ethers were shown to be recoverable from the feed of rats during evaluations of these retinoids for the suppression of mammary cancer (Shealy et al., 1997).

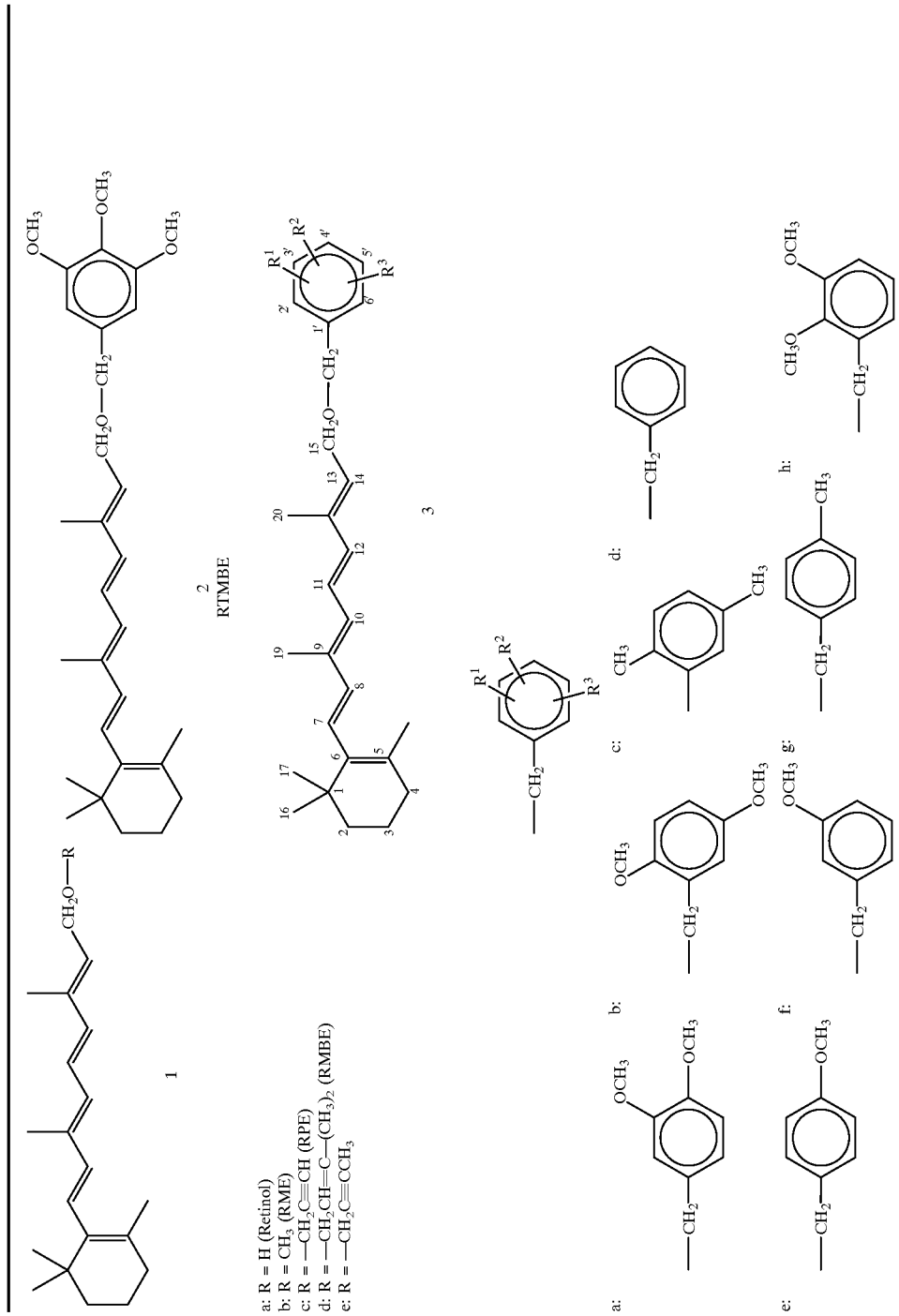

TABLE 1-continued
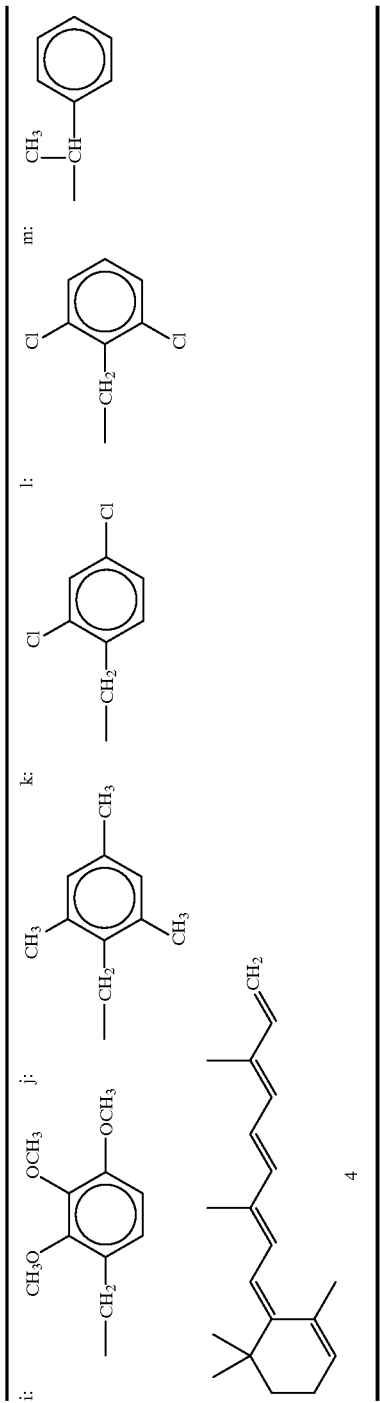

In a second aspect, the present invention provides a method for inhibiting breast cancer and/or breast cancer cell growth by administering an effective inhibitory amount of a compound of Formula I, optionally in combination with other anti-cancer agents. Thus, the present invention provides a method of inhibiting or preventing the growth of malignant cells by exposing cells to a compound of Formula I or physiologically acceptable salts thereof (also referred to herein as an active agent) or to a combination of a compound of Formula I and at least one other antineoplastic agent. This method is based on observations that compounds of Formula I are highly effective in preventing breast cancer in an animal model, as described in further details in the Examples. The breast cancer may be caused by chromosomal abnormalities, degenerative growth and developmental disorders, mitogenic agents, ultraviolet radiating (UV), viral infections, oncogenes, mutations in genes, inappropriate expression of a gene and presentation on a cell, or carcinogenic agent.

Administration of a pharmaceutical composition comprising the active agent encompassed by this invention may be for either a prophylactic or therapeutic use. When provided prophylactically, the active agent is provided in advance of any symptoms due to the cancer afflicting the individual. The prophylactic administration of the composition is intended as a chemopreventive therapy and serves to either prevent initiation of malignant cells or arrest or reverse the progression of transformed premalignant cells to malignant disease. When provided therapeutically the composition is provided at or after the onset of the disease. The therapeutic administration of the composition of this invention serves to attenuate or alleviate the cancer or facilitate regression of the cancer afflicting the individual. The term individual is intended to include any animal, preferably a mammal, and most preferably a human. Veterinary uses are intended to be encompassed by this definition.

In one embodiment of this invention, individuals at high risk for a cancer, or at high risk of reoccurrence of a cancer or who have known risk factors are prophylactically treated with the methods and compositions described herein. By way of example, such individuals may include those with a familial history for either early or late onset of breast cancer, individuals carrying deleterious mutations in the BRCA1 or BRCA2 gene, women at risk of occurrence of second primary breast carcinomas, women having genetic or other high risk factors or for post-disease prophylaxis. General ranges of suitable effective prophylactic dosages that may be used are about 0.1 mg/kg of body weight per day to about 1000 mg/kg/day, a preferred range is about 0.5 mg/kg/day to about 500 mg/kg/day, most preferred is about 1 mg/kg/day to about 100 mg/kg/day. The daily dose of the compound may be administered in a single dose or in portions at various hours of the day. Initially, a higher dosage may be required and may be reduced over time when the optimal initial response is obtained. By way of example, treatment may be continuous for days, weeks, or years, or may be at intervals with intervening rest periods.

The dosage may be modified in accordance with other treatments the individual may be receiving. One of skill in the art will appreciate that individualization of dosage may be required to achieve the maximum effect for a given individual. It is further understood by one skilled in the art that the dosage administered to a individual being treated may vary depending on the individuals age, severity or stage of the disease and response to the course of treatment. One skilled in the art will know the clinical parameters to evaluate to determine proper dosage for the individual being treated by the methods described herein.

The active agents of the present invention may also be used in combination with other antineoplastic agents, especially those with activity against breast cancer cells. As described above, the use of compounds of Formula I or physiologically acceptable salts thereof in combination with at least one other antineoplastic agent may be used in the prophylactic or therapeutic treatment of cancer. Examples of antineoplastic agents include, but are not limited to, drugs, chemicals, or hormones which prevent the initiation of malignant cells or inhibit or reverse the proliferation of malignant cells or prevent transformation of cells. In a particular embodiment hormonally sensitive cancers, such as some breast cancers, may be treated by the methods and compositions disclosed herein. By way of example, the estrogen receptor status of primary and metastatic breast cancer has been demonstrated to be of therapeutic and prognostic significance. Examples of hormonal modifying agents that have been used to prophylactically or therapeutically to treat breast cancers include, but are not limited to, the estrogen modifying drugs such as Tamoxifen and derivatives thereof (U.S. Pat. No. 4,536,516), Raloxifene and derivatives thereof (U.S. Pat. No. 4,418,068) and the like. Wiren a compound of Formula I is used in combination with another antineoplastic agent, the compound of Formula I may be administered prior to, concurrently or after the administration of the antineoplastic agent.

The dosing regimes and schedules used in clinical trials for testing of the antineoplastic agent may be used as a general guideline for doses of the antineoplastic agent to be used in combination with a compound of Formula I or a physiologically acceptable salt thereof. For example, in clinical trials Tamoxifen has been used in ranges of about 20 to 40 mg/day for periods ranging from less than one year to two years, the standard dose being about a 20 mg daily dose (Early Breast Cancer Trialists' Collaborative Group, 1988, 1992a, 1992b). Suggested dosages for Raloxifene and derivatives thereof are provided in U.S. Pat. No. 4,418,068. The general range of effective administration rates provided for Raloxifene and derivatives thereof is from about 0.05 mg/kg/day to about 50 mg/kg/day with a most highly preferred range of about 0.1 mg to about 5 mg/kg/day (U.S. Pat. No. 4,418,068). The dosing regimes and schedules used in clinical trials or provided in the literature may be used as a general guideline for doses of the estrogen modifying drug to be used in conjunction with compounds of Formula I. It is anticipated that a lower dosage for these estrogen modulating drugs may be effective when used in combination with compounds of Formula I. Examples of effective dosages for compounds of Formula I that may be used when combined with another antineoplastic agent are about 0.1 mg/kg/day to about 1,000 mg/kg/day, preferably about 0.5 mg/kg/day to about 500 mg/kg/day. Most preferred is about 1 mg/kg/day to about 100 mg/kg/day. One of skill in the art will appreciate that the dosage of the compound of Formula I and the dosage of the antineoplastic agent may need to be optimized for each individual. By way of example, compositions of a compound of Formula I and Tamoxifen or a compound of Formula I and Raloxifene may be used in the methods described herein. In yet another embodiment, a combination of a compound of Formula I, Tamoxifen and Raloxifene may be used in the methods described herein.

While it is possible for the composition comprising a compound of Formula I or physiologically acceptable salts alone or in combination with at least one other antineoplastic agent to be administered in a pure or substantially pure form or to administer each component in pure or substantially pure form, it is preferable to present it as a pharmaceutical composition, formulation or preparation. Thus, a third aspect of the present invention provides pharmaceutical compositions containing one or more of the compounds of Formula I, optionally also containing other anti-cancer agents. Pharmaceutical compositions containing a compound of the present invention as the active ingredient can be prepared according to conventional pharmaceutical compounding techniques. See, for example, *Remington's Pharmaceutical Sciences,* 18th Ed. (1990, Mack Publishing Co., Easton, Pa.). Typically, a preventative or therapeutically effective amount of active ingredient will be admixed with a pharmaceutically acceptable carrier. The carrier may take a wide variety of forms depending on the form of preparation desired for administration, e.g., intravenous, oral or parenteral. The compositions may further contain antioxidizing agents, stabilizing agents, preservatives and the like.

The formulations of the present invention, both for veterinary and for human use, comprise each component individually or as a composition as described above, together with one or more pharmaceutically acceptable carriers and, optionally, other therapeutic ingredients. The carrier(s) must be "acceptable" in the sense of being compatible with the other ingredients of the formulation and not deleterious to the recipient thereof The formulations may conveniently be presented in unit dosage form and may be prepared by any method well-known in the pharmaceutical art. Alternatively, the active agent may be added to food.

All methods include the step of bringing into association the active ingredient with the carrier which constitutes one or more accessory ingredients. In general, the formulations are prepared by uniformly and intimately bringing into association the active ingredient with liquid carriers or finely divided solid carriers or both, and then, if necessary, shaping the product into the desired formulation.

Formulations suitable for intravenous, intramuscular, subcutaneous, or intraperitoneal administration conveniently comprise sterile aqueous solutions of the active ingredient with solutions which are preferably isotonic with the blood of the recipient. Such formulations may be conveniently prepared by dissolving solid active ingredient in water containing physiologically compatible substances such as sodium chloride (e.g. 0.1–2.0M), glycine, and the like, and having a buffered pH compatible with physiological conditions to produce an aqueous solution, and rendering said solution sterile. These may be present in unit or multi-dose containers, for example, sealed ampoules or vials.

The formulations of the present invention may incorporate a stabilizer. Illustrative stabilizers are polyethylene glycol, proteins, saccharides, amino acids, inorganic acids, and organic acids which may be used either on their own or as admixtures. These stabilizers are preferably incorporated in an amount of 0.11–10,000 parts by weight per part by weight of each component or the composition. If two or more stabilizers are to be used, their total amount is preferably within the range specified above. These stabilizers are used in aqueous solutions at the appropriate concentration and pH. The specific osmotic pressure of such aqueous solutions is generally in the range of 0.1–3.0 osmoles, preferably in the range of 0.8–1.2. The pH of the aqueous solution is adjusted to be within the range of 5.0–9.0, preferably within the range of 6–8. In formulating each component separately or as a composition of the present invention, anti-adsorption agent may be used.

Additional pharmaceutical methods may be employed to control the duration of action. Controlled release preparations may be achieved through the use of polymer to complex or absorb the proteins or their derivatives. The controlled delivery may be exercised by selecting appropriate macromolecules (for example polyester, polyamino acids, polyvinyl, pyrrolidone, ethylenevinylacetate, methylcellulose, carboxymethylcellulose, or protamine sulfate) and the concentration of macromolecules as well as the methods of incorporation in order to control release. Another possible method to control the duration of action by controlled-release preparations is to incorporate the active agent or salt thereof alone or in combination with antineoplastic agents thereof into particles of a polymeric material such as polyesters, polyamino acids, hydrogels, poly(lactic acid) or ethylene vinylacetate copolymers.

Alternatively, instead of incorporating these agents into polymeric particles, it is possible to entrap these materials in microcapsules prepared, for example, by coacervation techniques or by interfacial polymerization, for example, hydroxy-methylcellulose or gelatin-microcapsules and poly-(methylmethacylate) microcapsules, respectively, or in colloidal drug delivery systems, for example, liposomes, albumin microspheres, microemulsions, nanoparticles, and nanocapsules or in macroemulsions.

When oral preparations are desired, the component may be combined with typical carriers, such as lactose, sucrose, starch, talc magnesium stearate, crystalline cellulose, methyl cellulose, carboxymethyl cellulose, glycerin, sodium alginate or gum arabic among others.

The administration of the compositions or of each individual component of the present invention may be for either a prophylactic or therapeutic purpose. The methods and compositions used herein may be used alone in prophylactic or therapeutic uses or in conjunction with additional therapies known to those skilled in the art in the prevention or treatment of cancer. Alternatively the methods and compositions described herein may be used as adjunct therapy. As adjunct therapy compounds of Formula I or physiologically acceptable salts thereof may be administered alone or in conjunction with an antineoplastic agent, such as Tamoxifen or derivatives thereof and/or Raloxifene or derivatives thereof.

EXAMPLES

The present invention is further detailed in the following Examples, which are offered by way of illustration and are not intended to limit the invention in any manner. Standard techniques well known in the art or the techniques specifically described below are utilized.

Example 1

General Materials and Methods

All operations involved in the preparation, isolation, purification, and transfer of retinoids were performed in an atmosphere, or under a current, of nitrogen or argon. All such operations were also performed in dim light or photographic darkroom light and, insofar as possible, with containers wrapped with aluminum foil or with black cloths. All retinoids were stored in an atmosphere of argon or nitrogen in hermetically sealed containers at $-20°$ C. or $-80°$ C. Commercial solutions of butyllithium were used. Chromatographic purifications were performed on columns of silica gel 60 or deactivated, neutral alumina. Deactivated alumina consisted of anhydrous neutral alumina and water mixed in proportions of 9:1.

Melting temperatures were determined in capillary tubes heated in a Mel-Temp apparatus. Ultraviolet spectra (UV)

were determined with absolute ethanol solutions and were recorded with a Perkin Elmer Model Lambda 9 spectrophotometer; maxima are given in nanometers. Mass spectral (MS) data were taken from low-resolution, electron-impact spectra determined at 70 eV with a Varian MAT Model 311A double-focusing spectrometer. The direct-probe temperature was 20° C. unless indicated otherwise; M=molecular ion. Some of the other peaks are identified as probable fragments, e.g., M minus a fragment. Proton nuclear magnetic resonance spectra ($^1$H-NMR) were determined at 300.635 MHZ and carbon-13 NMR spectra were determined at 75.602 MHZ with a Nicolet Model NT 300NB NMR spectrometer; tetramethylsilane was the internal reference. Assignments of chemical shifts are designated by the position numbers shown on structure 3. For $^1$H-NMR data, the multiplicity, the number of hydrogens, and the positions are given parenthetically with each chemical shift. The positions of the hydrogens are shown as HX (X=positions 1–21 or 2'–6'), and multiplicity is designated as follows: s=singlet, d=doublet, t=triplet, q=quartet, m=multiplet, dd=doublet of doublets, b=broad. Thin-layer chromatography (TLC) was performed on plates of fluorescing silica gel, and developed plates were examined with UV lamps (254 and 365 nm). Typically, chloroform was the developing solvent; chloroform-pentane (2:1) and cyclohexane-ethyl acetate (95:5) were also used. High-pressure liquid chromatography (HPLC) of synthesized retinoids was performed with components by Waters Associates systems and a Hewlett-Packard Model 3380-S integrator or with a Hewlett-Packard Model 1084B system. HPLC was performed on columns packed with octadecylsilylated silica (Spherisorb ODS), 5$\mu$ particle size. Unless indicated otherwise, the eluting solvent was 85:15 acetonitrile-1% aqueous ammonium acetate, isocratic, 1 mL/min flow rate; and elution was monitored by UV absorption at 340 nm. HPLC of biological samples was performed as stated below.

The benzyl chlorides used in the preparation of 2, 3c, 3e, 3f, 3j, 3k, and 3l and the benzyl bromides used in the preparation of 3d, 3g, and 3m were purchased from commercial sources. The benzyl bromides employed in the preparation of 3a, 3b, 3h, and 3i were prepared by treating the commercially available benzyl alcohols with phosphorus tribromide in anhydrous ether at 10° C. The products obtained from the brine-washed and dried ether solutions were dried further and used without further purification. 3,4,5-Trimethoxybenzyl bromide employed in the improved preparation of RTMBE was prepared by slowly passing hydrogen bromide through a dry benzene solution of commercially available 3,4,5-trimethoxybenzyl alcohol at 10–12° C. The product obtained from the washed (3 times with water, twice with saturated aqueous NaHCO$_3$, and twice with saturated aqueous NaCl) and dried ether solution was dried further and used without further purification.

Example 2

Preparation of Retinol

Retinol was prepared in a high degree of purity from commercial retinyl acetate for use as a reference retinoid in certain bioassays and as a precursor of retinyl ethers. A solution of 100 g of commercial all-trans-retinyl acetate in 1.5 L of a methanol solution of sodium hydroxide (2%) was stirred under a nitrogen atmosphere at room temperature. After 2 h, retinyl acetate was not observable by TLC. The orange solution was concentrated under reduced pressure, and at 30° C., to about 300 mL; the concentrated solution was poured, with stirring, into cold water (1.5 L); and hexane (1 L) was added to dissolve the precipitated retinol. The organic layer was separated and washed with three portions of water, saturated aqueous NaCl being added (as required) to separate emulsions. The organic solution was washed further with saturated aqueous NaCl, dried (MgSO$_4$), and concentrated under reduced pressure to an orange syrup. A solution of the syrup in ethyl formate (100 mL) was cooled to −20° C., seeded with pure retinol, and stored (under a nitrogen atmosphere) at −20° C. The crystalline retinol was collected by filtration under nitrogen, washed with cold (−70° C.) ethyl formate, and dried in vacuo: yield, 47 g (54%); mp 60–62° C. [lit. Robeson et al., 1955), 62–64° C.]; HPLC, 99.4%: UV $\lambda$max 325 ($\epsilon$ 53 000) and 250 nm ($\epsilon$ 5000); $^1$H NMR in accord with the structure.

Some of the specimens of commercial retinyl acetate contained small amounts of 13-cis-retinyl acetate (2–4%). The crude retinol (orange syrup, obtained in yields of 85–93%) was usually used without further purification for the preparation of large amounts of the retinyl ethers. The latter compounds were then purified as described below.

Example 3

Synthesis of Retinyl 3,4,5-Trimethoxybenzyl Ether (2, RTMBE)

Retinol (42 g, 147 mmol) was dissolved in anhydrous benzene (400 mL), and the solution was cooled to 10° C. A solution of n-butylithium in hexane (90 mL, 1.6 molar) was added to the cold, stirred retinol solution until a dark red color persisted. The resulting solution was stirred for about 0.25 hr and then added in a slow stream to a stirred solution of 3,4,5-trimethoxybenzyl chloride (35 g, 166 mmol) in dry DMF (400 mL). The reaction mixture was heated slowly to 80° C. and was maintained at that temperature for about 2 hr. The reaction mixture was cooled to room temperature and poured into a mixture of water, ice, and ether. After the total mixture had been thoroughly agitated, the organic layer was separated, and the aqueous layer was extracted with ether. The ether extract was combined with the original organic layer. The total organic solution was washed with water and then with brine, dried with magnesium sulfate, and concentrated to an orange syrup (about 67 g). The crude product was divided into three approximately equal portions of 22 g, and each portion was subjected to flash chromatography on a column of silica gel 60 with hexane-ethyl acetate (3: 1) as the eluting solvent. The course of the elution was monitored by TLC. Fractions from each of the three columns that exhibited only one spot on thin-layer chromatograms were combined, and the resulting solution was concentrated in vacuo to a yellow syrup; weight 21 g. The less pure fractions were combined and subjected to flash chromatography as stated above. This process was repeated until additional purified portions (10 g and 5 g) were obtained. (The chromatographic operations removed unreacted 3,4,5-trimethoxybenzyl chloride, bis(3,4,5-trimethoxybenzyl) ether, anhydroretinol, and other unidentified impurities.) The three purified portions were combined in ethanol, this solution was concentrated in vacuo to a syrup, the process of dissolution in ethanol and evaporation of the solvent was repeated to facilitate the removal of small amounts of the eluting solvents, and the residual syrup was kept in vacuo until it reached a constant weight: 35 g (52% yield); HPLC monitored at 340 nm, 99.6%; HPLC monitored at 254 im, 99.2%; UV $\lambda_{max}$ 326 nm ($\epsilon$ 51 600), 318 nm (shoulder), 225 nm (shoulder); $^1$H NMR (CDCl$_3$) $\delta$ 6.61 (dd, 1H, H11, $J_{10,11}$=11.1 Hz, $J_{11,12}$=15.1 Hz), 6.58 (s, 2H, H2',H6'), 6.31 (d, 1H, H12), 6.16 (bd, 1H, H8), 6.11 (d, 1H, H7,$J_{7,8}$=16.5

Hz), 6.10 (d, 1H, H10), 5.69 (t, 1H, H14), 4.45 (s, 2H, H21), 4.20 (d, 1H, H15,$J_{14,15}$=7.0 Hz), 3.87 (s, 6H, OCH$_3$), 3.84 (s, 3H, OCH$_3$), 2.01 (t, 2H, H4), 1.96 (d, 3H, H19, $J_{10,19}$=0.8 Hz), 1.85 (s, 3H, H20), 1.71 (s, 3H, H18), 1.65–1.57 (m, 2H, H3), 1.48–1.44 (m, 2H, H2), 1.02 (s, 6H, H16, H17).

Example 4

General Procedure for the Preparation of Retinyl Benzyl Ethers (3)

A solution of crystalline retinol (5 g, 17.5 mmol) in dry benzene (50 mL) was cooled to 10° C. A solution of n-butyllithium in hexane (1.6 M, about 12 mL) was added to the cold, stirred retinol solution until a dark red color persisted. The resulting solution was stirred for 0.25 hr, and a solution of the appropriate benzyl halide (26–34 mmol) in dry DMF (950 mL) was added to the lithium retinoxide solution. The stirred reaction mixture was allowed to warm to room temperature. The progress of the reaction was monitored by analyzing aliquot portions by TLC to determine when the reaction was complete, or almost complete, and to determine whether the temperature of the reaction mixture should be raised. The time allowed for a reaction to continue and the chosen temperature were based on these TLC determinations. The reaction mixture was cooled in an ice bath and then poured into cold water; the aqueous mixture was extracted twice with ether; and the ether extract (two portions combined) was washed with brine, dried (MgSO$_4$), and concentrated under reduced pressure to a yellow syrup.

Usually, the first stage of the purification of the crude product was gravity chromatography either on a column of silica gel 60 with chloroform as the developing and eluting solvent or on a column of deactivated alumina with pentane followed by pentane-ethyl acetate (95:5) as the eluting solvents. Flash chromatography on silica gel 60 with chloroform or a chloroform-hydrocarbon solution (pentane, hexane, or cyclohexane) as the eluting solvent was also used for the first-stage in the purification process. Eluent portions were analyzed by TLC, and those fractions that appeared to contain only the desired retinyl ether were combined and concentrated to a syrup. Less pure fractions that consisted principally of the desired retinyl ether were combined and subjected to successive chromatographic operations on silica gel 60 or on deactivated alumina by repeating the first-stage chromatographic procedures or by varying the proportions of chloroform-hydrocarbon or hydrocarbon-ethyl acetate solvent mixtures. Purified fractions from the initial and the subsequent chromatographic procedures were combined in ethanol or ether and the solvents were evaporated under reduced pressure. Most of the retinyl benzyl ethers were yellow syrups.

Initial specimens of the various retinyl benzyl ethers were obtained by the procedure described above. When larger quantities of a retinyl ether were needed for chemoprevention studies in vivo and for toxicological and pharmacological studies, the general procedure was employed on a larger scale. The preparation and purification of 3a–3e illustrate the general procedure.

Example 5

Synthesis of Retinyl 3,4-Dimethoxybenzyl Ether (3a)

A solution of purified retinol (5 g, 17.5 mmol) in benzene (60 mL) was concentrated in vacuo to about 50 mL (in order to remove azeotropically any water that might be present) and then was cooled to 10° C. A solution of butyllithium in hexane (1.6 M, ca. 12 mL) was added to the cold, stirred retinol solution until a dark red color persisted. The resulting solution was stirred for 0.25 hr, and a solution of 3,4-dimethoxybenzyl bromide (6 g, 26 mmol) in anhydrous DMF (50 mL) was added in one portion to the lithium retinoxide solution. The stirred reaction mixture was allowed to warm slowly to room temperature, warmed to 35–40° C., maintained at that temperature for 2 hr, cooled, and poured into cold water. The aqueous mixture was extracted twice with ether. The ether extract (two portions combined) was washed with brine, dried (MgSO$_4$), and concentrated to a yellow syrup (wt, 7 g). The crude product was purified by chromatography on a column of silica gel 60 with chloroform as the eluting solvent. Elution of the desired product was monitored by TLC. The best fractions were combined and the solvent was evaporated under reduced pressure: weight of residual syrup, 2.1 g; HPLC, 99.5%. Less pure fractions were combined and subjected to chromatography as stated above: HPLC of the purified residual syrup: 99% at 340 nm, 100% at 254 nm. The two portions were combined in ethanol, and the solvent was evaporated: yield of yellow syrup, 3.5 g (46%); MS mn/z 436 (M), 285 ($C_{20}H_{29}O$), 269 ($C_{20}H_{29}$), 255 ($C_{19}H_{27}$), 151 (3,4-dimethoxybenzyl); $\lambda_{max}$327 im ($\epsilon$ 52 600), 231 mn ($\epsilon$ 13 200), $\epsilon$ calculated for $C_{29}H_{40}O_3 \cdot \frac{3}{4}C_2H_5OH$; $^1$H NMR (CDCl$_3$) $\delta$ 6.91 (d, 1H, H2', $J_{2',6'}$=1.8 Hz), 6.87 (dd, 1H, H6', $J_{6',2'}$=1.8Hz, $J_{5',6'}$=8.1 Hz), 6.83 (d, 1H, H5', $J_{6',5'}$=8.1 Hz), 6.59 (dd, 1H, H11, $J_{11,12}$=15.2 Hz, $J_{10,11}$=11.2 Hz),6.30 (d, 1H, H12), 6.15 (bd, 1H, H8, $J_{7,8}$=16.2 Hz), 6.10 (d, 1H, H7), 6.09 (bd, 1H, H10), 5.68 (bt, 1H, H14),4.46 (s, 2H, H21), 4.16 (d, 2H, H15, J=6.8 Hz), 3.89 (s, 3H, OCH$_3$), 3.87 (s, 3H, OCH$_3$), 2.02 (t, 2H, H4), 1.95 (d, 3H, H19, $J_{10,19}$=0.7 Hz), 1.83 (bs, 3H, H20), 1.71 (s, 3H, H18), 1.65–157 (m, 2H, H3), 1.48–1.44 (m, 2H, H2), 1.02 (s, 6H, H16, H17). Anal. Calcd. for $C_{29}H_{40}O_3 \cdot \frac{3}{4}C_2H_5OH$: C, 77.70; H, 9.52. Found: C, 77.96; H, 9.43.

Example 6

Synthesis of Retinyl 2,5-Dimethoxybenzyl Ether (3b)

Retinyl 2,5-Dimethoxybenzyl Ether (3b) was prepared from retinol and 2,5-dimethoxybenzyl bromide according to the procedure for 3a. The crude product was subjected to chromatography in chloroform on a column of silica gel 60. Successive chromatographic purifications of eluted portions were performed on columns of silica gel 60 with chloroform, 7:3 hexane-ethyl acetate, or 1:1 chloroform-hexane as eluting solvents. The progress of the purification of the original crude product and of fractions from the successive chromatographic operations was monitored by TLC and HPLC. The purified specimens from each chromatographic procedure were combined in ethanol, and the ethanol solution was concentrated in vacuo to a yellow syrup: yield, 16%; HPLC, 100%; MS m/z 436 (M), 285 ($C_{20}H_{29}O$), 269 ($C_{20}H_{29}$),255 ($C_{19}H_{17}$),151 (2,5-dimethoxybenzyl); UV $\lambda_{max}$326 um ($\epsilon$ 51 600),225 nm ($\epsilon$ 12 600), $\epsilon$ calculated for $C_{29}H_{40}O_3 \cdot C_2H_5OH$; $^1$H NMR (CDCl$_3$) $\delta$ 6.99 (bs, 1H, H6'), 6.80 (d, 1H, H3', $J_{3',4'}$=8.1 Hz), 6.77 (dd, 1H, H4', $J_{4',6'}$=1.5 Hz), 6.59 (dd, 1H, H11, $J_{10},$11=11.0 Hz, $J_{11,12}$=15.1 Hz), 6.30 (d, 1H, H12), 6.16 (bd, 1H, H8, $J_{7,8}$=16.1 Hz), 6.10 (d, 1H, H7), 6.09 (d, 1H, H10), 5.71 (t, 1H, H14), 4.54 (s, 1H, H21), 4.23 (d, 2H, H15, $J_{14,15}$=6.7 Hz), 3.79 (s, 3H, OCH$_3$), 3.77 (s, 3H, OCH$_3$), 2.01 (t, 2H, H4), 1.95 (d, 3H, H19, $J_{10,19}$=0.7 Hz), 1.85 (d, 3H, H20, $J_{14,20}$=0.8 Hz), 1.71 (s, 3H, H18), 1.65–1.57 (m, 2H, H3), 1.48–144 (m, 2H, H2), 1.02 (s, 6H, H16, H17). Anal. Calcd. for $C_{29}H_{40}O_3 \cdot C_2H_5OH$: C, 77.15; H, 9.61. Found: C, 77.16; H, 9.23.

Example 7

Synthesis of Retinyl 2,5-Dimethylbenzyl Ether (3c)

Retinyl 2,5-Dimethylbenzyl Ether (3c) was prepared from retinol and 2,5-dimethylbenzyl chloride as outlined by the general procedure. The reaction mixture was stirred at room temperature during 2 hr and at 80° C. during 3 hr. After the crude product had been obtained from the ether extract, successive chromatographic operations were performed on silica gel 60 as follows: flash chromatography with 2:1 chloroform-pentane; flash chromatography with 95:5 cyclohexane-ethyl acetate; gravity chromatography with 97:3 cyclohexane-ethyl acetate. The product obtained by combining the purified specimens from each chromatographic procedure was a syrup: yield, 30%; HPLC (at 340 nm or 254 nm), 100%; MS m/z 404 (M), 285 ($C_2OF_{29}O$), 269 ($C_{20}H_{29}$), 255 ($C_{19}H_{27}$), 119 (2,5-dimethylbenzyl); UV $\lambda_{max}$326 nm (ε 50 800), 251 (6100); $^1$H NMR (CDCl$_3$) δ 7.14 (bs, 1H, H6'), 7.04 (bd, 1H, H3', $J_{3',4'}$=7.7 Hz), 7.00 (dd, 1H, H4', $J_{4',6'}$=1.6 Hz), 6.60 (dd, 1H, H11, $J_{10,11}$=11.1 Hz, $J_{11,12}$=15.1 Hz), 6.31 (d, 1H, H12), 6.15 (d, 1H, H8, $J_{7,8}$=16.2 Hz), 6.11 (d, 1H, H7), 6.09 (d, 1H, H10), 5.70 (t, 1H, H14), 4.48 (s, 2H, H21), 4.20 (d, 2H, H15, $J_{14,15}$=6.8 Hz), 2.31 (s, 3H, CH$_3$), 2.29 (s, 3H, CH$_3$), 2.01 (t, 2H, H14), 1.95 (d, 3H, H19, $J_{10,19}$=0.6 Hz), 1.85 (bs, 3H, H20), 1.71 (s, 3H, H18), 1.65–1.57 (m, 2H, H3), 1.48–1.44 (m, 2H, H2), 1.02 (s, 6H, H16, H17). Anal. Calcd. for $C_{29}H_{40}O$: C, 86.08; H, 9.96. Found: C, 85.75; H, 10.32.

Example 8

Synthesis of Retinyl Benzyl Ether (3d)

Retinyl Benzyl Ether (3d) was prepared from retinol and benzyl bromide as outlined by the general procedure. Successive chromatographic operations were performed with the following columns and eluting solvents: deactivated alumina and pentane followed by pentane-ethyl acetate (95:5); repetition of this procedure; silica gel 60 and chloroform; repetition of the latter method. Eluent fractions that contained pure 3d were combined and concentrated to a yellow syrup: yield, 33%; HPLC, 100%; MS m/z 376 (M), 285 ($C_{20}H_{29}O$), 269 ($C_{20}H_{29}$), 255 ($C_{19}H_{17}$), 91 (benzyl); UV $\lambda_{max}$326 nm (ε 50 400), 251 nm (5900); $^1$H NMR (CDCl$_3$) δ 7.37–7.27 (m, 5H, $C_6H_5$), 6.59 (dd, 11H, H11, $J_{10,11}$=11.2 Hz, $J_{11,12}$=15.1 Hz), 6.30 (d, 1H, H12), 6.15 (d, 1H, H8, $J_{7,8}$=16.4 Hz), 6.11 d, 1H, H7), 6.10 (d, 1H, H10), 5.69 (t, 1H, H14), 4.52 (s, 2H, H21), 4.18 (d, 2H, H15, $J_{14,15}$=6.9 Hz), 2.01 (t, 2H, H4), 1.95 (d, 3H, H19, $J_{10,19}$=0.8 Hz), 1.83 (bd, 3H, H20, $J_{14,20}$=0.8 Hz), 1.71 (s, 3H, H18), 1.65–1.57 (m, 2H, H3), 1.48–1.44 (m, 2H, H2), 1.02 (s, 6H, H16, H17). Anal. Calcd. for $C_{27}H_{36}O \cdot \frac{1}{3}H_2O$: C, 84.76; H, 9.57. Found: C, 84.50; H, 9.71.

Example 9

Synthesis of Retinyl 4-Methoxybenzyl Ether (3e)

Retinyl 4-Methoxybenzyl Ether (3e) was prepared from retinol and 4-methoxybenzyl chloride by the method described for 3c. The ether extract was washed successively with saturated sodium bicarbonate solution and with brine. The crude product was purified by successive chromatographic operations with the column absorbent and eluting solvent as follows: deactivated alumina, pentane and then 95:5 pentane-ethyl acetate; silica gel 60, chloroform; silica gel 60, 4:1 chloroform-pentane; repetition of the last method. The purified product was a yellow syrup: HPLC, 99.3% (340 nm), 100% (254 nm); MS m/z 406 (M), 285 ($C_{20}H_{29}O$), 269 ($C_{20}H_{29}$), 255 ($C_{19}H_{27}$), 121 (4-methoxybenzyl); UV $\lambda_{max}$326 nm (ε 51 300), 226 nm (ε 14 000); $^1$H NMR (CDCl$_3$) δ 7.27 (m, 2H, H2'), 6.88 (m, 2H, H3'), 6.59(dd, 1H, H11, $J_{10,11}$=11.3 Hz, $J_{11,12}$=15.0Hz), 6.29 (d, 1H, H12), 6.15 (bd, 1H, H8, $J_{7,8}$=16.0Hz), 6.11 (d, 1H, H7), 6.09 (d, 11H, H10), 5.68 (t, 1H, H14), 4.45 (s, 2H, H21), 4.15 (d, 2H, H15, $J_{14,15}$=6.8 Hz), 3.80 (s, 3H, OCH$_3$), 2.01 (t, 2H, H4), 1.95 (s, 3H, H17), 1.82 (s, 3H, H20), 1.71 (s, 3H, H18), 1.65–1.57 (m, 2H, H3), 1.48–1.44 (m, 3H, H2), 1.02 (s, 6H, H16, H17). Anal. Calcd. for $C_{28}H_{38}O_2 \cdot \frac{1}{2}H_2O$:C, 80.92; H, 9.46. Found: C, 80.93; H, 9.38.

A similar run with 50 g (175 mmol) of retinol and 32 g (204 mmol) of 4-methoxybenzyl chloride furnished an orange syrup from the ether extract. This crude product was chromatographed on deactivated neutral alumina (95:5 $Al_2O_3$—$H_2O$) with 95:5 pentane-ethyl acetate as the eluting solvent. Eluent portions that contained 3e were combined and concentrated to a yellow syrup: yield 50.5 g (71%); HPLC, 99.8% (340 nm), 98% (254 nm).

Example 10

Synthesis of Retinyl 3-Methoxy Benzyl Ether (3f)

Retinyl 3-Methoxy Benzyl Ether (3f) was prepared from retinol and 3-methoxybenzyl chloride by the procedure described for 3c. The crude product was chromatographed on a column of deactivated alumina with pentane and then pentane-ethyl acetate (95:5) as eluting solvents. The best fractions, identified by TLC, were combined, concentrated to a syrup, and chromatographed on silica gel 60 with chloroform as the eluting solvent. Fractions that appeared to be pure (TLC) were combined and concentrated to a yellow syrup that crystallized: yield, 56%; HPLC, 100%; mp 41–42° C.; MS m/z 406 (M), 285 ($C_{20}H_{29}O$), 269 ($C_{20}H_{29}$), 255 ($C_{19}H_{27}$), 121 (3-methoxybenzyl); UV $\lambda_{max}$326 nm (ε 50 200); $^1$H NMR (CDCl$_3$) δ 7.26 (t, 1H, H5', $J_{4',5'}$=8.1 Hz, $J_{5',6'}$=8.1 Hz), 6.92 (m, 2H, H2', H4'), 6.83 (m, 1H, H6'),6.60 (dd, 1H, $J_{10,11}$=11.2 Hz, $J_{11,2}$=15.1 Hz), 6.30 (d, 1H, H12), 6.16 (d, 1H, H8, $J_{7,8}$=16.3 Hz), 6.11 (d, 1H, H7), 6.10 (d, 1H, H10), 5.69 (t, 1H, H14), 4.50 (s, 2H, H21), 4.18 (d, 2H, H15, $J_{14,15}$=6.9 Hz), 3.81 (s, 3H, OCH$_3$), 2.01 (t, 2H, H4),1.95 (s, 3H, H19), 1.83 (s, 3H, 1120), 1.71 (s, 3H, H18), 1.65–1.57 (m, 2H, H3), 1.48–1.44 (m, 2H, H2), 1.02 (s, 6H, H16, H17). Anal. Calcd. for $C_{28}H_{38}O_2 \cdot \frac{1}{39}H_2O$: C, 81.51;H, 9.45. Found: C, 81.67;H, 9.20.

Example 11

Synthesis of Retinyl 4-Methylbenzyl Ether (3g)

A mixture of lithium retinoxide, benzene, DMF, and 4-bromotoluene, prepared as described by the general procedure, was stirred at room temperature for 5 hr. Compound 3g was obtained from the crude product (isolated and purified by the methods outlined in the general procedure): 38% yield; HPLC, 99.6%; MS m/z 390 (M), 285 ($C_{20}H_{29}$), 269 ($C_{20}$H29), 255 ($C_{19}H_{27}$), 105 (4-methylbenzyl); UV $\lambda_{max}$326 nm, (ε 48 900), 251 nm (ε 6300); $^1$H NMR (CDCl$_3$) δ 7.24 (d, 2H, H2, H6, $J_{2,3}$=8.0 Hz), 7.15 (d, 2H, H3, H5), 6.59 (dd, 1H, H11, $J_{10,11}$=11.2 Hz, $J_{11,12}$=15.2 Hz), 6.29 (d, 1H, H12), 6.15 (d, 1H, H8), 6.11 (d, 1H, H7, $J_{7,8}$=16.0 Hz), 6.10 (d, 1H, H10), 5.68 (t, 1H, H14), 4.48 (s, 2H, H15, $J_{14,15}$=6.9 Hz), 2.34 (s, 3H, 4'—CH$_3$), 2.01 (t, 2H, H4),1.95 (d, 3H, H19, $J_{10,19}$=0.7 Hz), 1.82 (s, 3H, H20), 1.71 (s, 3H, H18), 1.65–1.57 (m, 2H, H3), 1.48–1.44 (m, 2H, H2), 1.02 (s, 6H, H16, H17). Anal. Calcd. for C$_{28}$H$_{38}$O:C, 86.10; H, 9.81. Found: C, 86.01; H, 9.90.

Example 12

Retinyl 2,3-Dimethoxybenzyl Ether (3h) was prepared from 2,3-dimethoxybenzyl bromide by the procedure described for the preparation of 3a. The crude product was chromatographed on a column of deactivated alumina with pentane and then 9:1 pentane-ethyl acetate as eluting solvents. Eluent portions, identified by TLC, that contained 3h were combined and concentrated to a yellow solid. Less pure fractions were combined and chromatographed on deactivated alumina with 9:1 pentane-ethyl acetate as the eluting solvent. Purified 3h obtained from the second column was combined with that from the first, and the combined material was triturated with methanol: yield of yellow solid, 39%; HPLC, 100% (340 or 254nm); mp 58–60° C.; MS m/z 436 (M), 285 (C$_{20}$H$_{29}$O), 269 (C$_{20}$ H$_{29}$), 255 (C$_{19}$H$_{27}$), 151 (2,3-dimethoxybenzyl); UV $\lambda_{max}$326 nm ($\epsilon$ 53 700), 252 nm ($\epsilon$ 6200); $^1$H NMR (CDCl$_3$) $\delta$ 7.05 (t, 9H, 5'), 7.00 (dd, 1H, H6', $J_{5',6'}$=7.7 Hz, $J_{4',6'}$=1.9 Hz), 6.87 (dd, 1H, H4', $J_{4',5'}$=7.6 Hz), 6.59 (dd, 1H, H11, $J_{10,11}$=11.2 Hz, $J_{11,12}$=15.0 Hz), 6.30 (d, 1H, H12), 6.15 (d, 1H, H8), 6.11 (d, 1H, H7, $J_{7,8}$=16.0 Hz), 6.09 (d, 1H, H10), 5.70 (t, 1H, H14),4.58 (s, 2H, H21),4.21 (d, 2H, H$_{15}$, $J_{14,15}$=6.7 Hz), 3.86 (s, 3H, OCH$_3$), 3.84 (s, 3H, OCH$_3$), 2.01 (t, 2H, H4), 1.95 (s, 3H, H19), 1.84 (s, 3H, H20), 1.71 (s, 3H, H18), 1.65–1.57 (m, 2H, H3), 1.48–1.44 (m, 2H, H2), 1.02 (s, 6H, H16, H17). Anal. Calcd. for C$_{29}$H$_{40}$O$_3$: C, 79.77; H, 9.23. Found: C, 79.59; H, 9.33.

Example 13

Synthesis of Retinyl 2,3,4-Trimethoxybenzyl Ether (3i)

Retinyl 2,3,4-Trimethoxybenzyl Ether (3i) was prepared by the procedure described for the preparation of 3a, but the total crude product was purified by chromatography on a column of deactivated alumina with pentane and then pentane-ethyl acetate (4:1) as eluting solvents. Pure 3i was obtained by combining the best fractions and chromatographing the combined material on a column of silica gel 60 with chloroform-pentane (4:1) as eluting solvent: yield, 33%; HPLC, 100% (340 or 254 nm); MS m/z 466 (M), 285 (C$_{20}$H$_{29}$O), 269 (C$_{20}$H$_{29}$), 255 (C$_{19}$H$_{17}$), 181 (2,3,4-trimethoxybenzyl), 166 (181-CH$_3$); UV $\lambda_{max}$326 ($\epsilon$ 50 900); $^1$H NMR (CDCl$_3$) 7.04 (d, 1H, H5', $J_{5',6'}$=8.6 Hz), 6.06 (d, 1H, H6'), 6.59 (dd, 1H, H11, $J_{10,11}$=11.1 Hz, $J_{11,12}$=15.1 Hz), 6.30 (d, 1H, H12), 6.15 (d, 1H, H8, $J_{7,8}$=16.2 Hz), 6.11 (d, 1H, H7), 6.10 (d, 1H, H10), 5.69 (t, 1H, H14), 4.48 (s, 2H, H21), 4.19 (d, 2H, H15, $J_{14,15}$=6.8 Hz), 3.90 (s, 3H, OCH$_3$), 3.87 (s, 3H, OCH$_3$), 3.86 (s, 3H, OCH$_3$), 2.01 (t, 2H, H4), 1.95 (d, 3H, H19, $J_{10,19}$=0.8 Hz), 1.85 (s, 3H, H20), 1.71 (m, 3H, H18), 1.65–1.57 (m, 2H, H3), 1.48–1.44 (m, 2H, H2), 1.02 (s, 6H, H16, H17). Anal. Calcd. for C$_{30}$H$_{42}$O$_4$: C, 77.21; H, 9.07. Found: C, 77.14; H, 9.18.

Example 14

Synthesis of Retinyl 2,4,6-Trimethylbenzyl Ether 3j

Retinyl 2,4,6-Trimethylbenzyl Ether (3j) was prepared from retinol and 2,4,6-trimethylbenzyl chloride by the method described for 3c and was purified by flash-chromatography with the following columns and eluting solvents: silica el 60 with cyclohexane-chloroform (3:1), repetition of this method, and silica gel 60 with chloroform: yield, 19%; HPLC, 99.8%; UV $\lambda_{max}$326 nm ($\epsilon$ 51 900); $^1$H NMR (CDCl$_3$) $\delta$ 6.83 (bs, 2H, H3'), 6.59 (dd, 1H, H11, $J_{10,11}$=11.1 Hz, $J_{11,12}$=15.2 Hz, 6.30 (d, 1H, H12), 6.16 (bd, 1H, H8, $J_{7,8}$=16.5 Hz), 6.10 (d, 1H, H7), 6.09 (d, 1H, H10), 5.69 (t, 1H, H14), 4.50 (s, 2H, H21),4.18(d, 2H, H15, $J_{14,15}$=6.8 Hz), 2.35 (s, 6H, 2'—CH$_3$),2.25 (s, 3H, 4'—CH$_3$), 2.01 (t, 2H, H4), 1.95 (d,3H, H19, $J_{10,19}$=0.8 Hz), 1.86 (s, 3H, H20), 1.70 (s, 3H, H18),1.65–1.57 (m, 2H, H3), 1.48–1.44 (m, 2H,H4), 1.02 (s, 6H, H16, H17). Anal. Calcd. for C$_{30}$H$_{42}$O.⅓H$_2$O: C, 84.85;H, 10.13. Found C, 84.92; H, 10.13.

Example 15

Synthesis of Retinyl 2,4-Dichlorobenzyl Ether (3k)

Retinyl 2,4-Dichlorobenzyl Ether (3k) was prepared from retinol and 2,4-dichlorobenzyl chloride by the method described for 3c and was purified by flash-chromatography on silica gel 60 with cyclohexane-chloroform (2:1) as eluting solvent and then repetition of this method: yield, 32%; HPLC, 100%; UV $\lambda_{max}$326 nm ($\epsilon$ 49400), 251 ($\epsilon$ 5700); $^1$H NMR (CDCl$_3$) $\delta$ 7.44 (d, 1H, H6', $J_{5',6'}$=8.2 Hz), 7.37 (d, 1H, H3', $J_{3',5'}$=2.2 Hz), 7.25 (dd, 1H, H5', $J_{5',6'}$=8.2 Hz, $J_{3',5'}$=2.2 Hz),6.62(dd, 1H, H11, $J_{10,11}$=11.2 Hz, $J_{11,15}$=15.1 Hz), 6.30 (d, 1H, H12) 6.16 (bd, 1H, H8, $J_{7,8}$=16.4 Hz), 6.11 (d, 1H, H7), 6.10 (d, 1H, H10), 5.69 (t, 1H, H14), 4.57 (s, 2H, H21), 4.25 (d, 2H, H15, $J_{14,15}$=6.8 Hz), 2.01 (t, 2H, H4), 1.96 (d, 3H, H19, $J_{10,19}$=0.7 Hz), 1.86(s, 3H, H20),1.71 (s,3H, H18),1.65–1.57 (m, 2H, H3),1.48–1.44 (m, 2H, H2), 1.03 (s, 6H, H16, H17). Anal. Calcd. for C$_{27}$H$_{34}$Cl$_2$O: C, 72.80; H, 7.69. Found: C, 72.33; H, 7.85.

Example 16

Synthesis of Retinyl 2,6-Dichlorobenzyl Ether (3l)

Retinyl 2,6-Dichlorobenzyl Ether (3l) was prepared from 2,6-dichlorobenzyl bromide as outlined for 3g. Purification of the crude product was effected by successive gravity chromatographic operations with deactivated alumina and 9:1 pentane-ethyl acetate, silica gel 60 and 1:1 pentane-chloroform, silica gel and cyclohexane followed followed by flash chromatography with silica gel 60 and chloroform and then with silica gel 60 and 95:5 cyclohexane-ethylacetate: yield, 19%; HPLC, 99.4%; MS m/z 444 (M), 285 (C$_2$OH$_{29}$O), 269 (C$_2$OH$_{29}$), 255 (C$_{19}$H$_{17}$),159 (2,6-dichlorobenzyl); UV $\lambda_{max}$ (327 nm ($\epsilon$ 50 300), 251 nm (6100); $^1$H NMR (CDCl$_3$) $\delta$ 7.31 (m, A part of an A$_2$ B spin system, 2H, H3', H5'), 7.18 (m, B part of an A$_2$B spin system, 1H, H4'), 6.60 (dd, 1H, H11, $J_{10,11}$=11.1 Hz, $J_{11,12}$=15.1 Hz), 6.29 (d, 1H, H12), 6.15 (bd, 1H, H8), 6.10 (d, 1H, H7, $J_{7,8}$=16.2 Hz), 6.09 (bd, 1H, H10), 5.71 (t, 1H, H14), 4.77 (s, 2H, H21),4.26 (d, 1H, H15, $J_{14,15}$=6.9 Hz), 2.01 (t, 2H, H4),1.95 (d, 3H, H19, $J_{10,19}$=0.5 Hz), 1.87 (s, 3H, H20), 1.71 (s, 3H, H18), 1.65–1.57 (m, 3H, H3), 1.48–1.44 (m, 2H, H2), 1.02 (s, 6H, H16, H17). Anal. Calcd. for C$_{27}$H$_{34}$Cl$_2$O: C, 72.80; H, 7.69. Found: C, 72.67; H, 7.98.

Example 17

Synthesis of Retinyl α-Methylbenzyl Ether (3m)

Retinyl α-Methylbenzyl Ether (3m) was prepared from a-methylbenzyl bromide by the general procedure, but the reaction mixture was stirred at 70–80° C. for 6 hr and then at room temperature overnight. The product was isolated by flash chromatography as follows: silica gel 60 with chloroform as the eluting solvent, repetition of this method, and silica gel 60 with 1:1 cyclohexane-chloroform as eluting solvent: HPLC, 99.8%; $^1$H NMR (CDCl$_3$) δ 7.37–7.24 (m, 5H, C$_6$H$_5$), 6.56 (dd, 1H, H11, $J_{10,11}$=11.1 Hz, $J_{11,12}$=15.0 Hz), 6.28 (d, 1H, H12), 6.14 (d, 1H, H8), 6.10 (d, 1H, H7, $J_{7,8}$=16.2 Hz), 6.10 (bd, 1H, H10), 5.65 (t, 1H, H14), 4.45 (q, 1H, H21, $J_{21,CH_3}$=6.8 Hz), 4.01 (dd, 1H, H15a, $J_{14,15a}$=6.6 Hz, $J_{15a,15b}$=12.6 Hz), 3.97 (dd, 1H, H15b, $J_{14,15b}$=7.1 Hz), 2.01 (t, 2H, H4), 1.94 (d, 3H, H19, $J_{10,19}$=0.7 Hz), 1.73 (d,3H, H20, $J_{14,10}$=0.6 Hz), 1.71 (s, 3H, H18), 1.65–1.57 (m, 2H, H3), 1.48–1.44 (m, 2H, H2), 1.45 (d,3H, 21—CH$_3$, $J_{21,CH_3}$=6.5 Hz), 1.02 (s, 6H, H16, H17). Anal. Calcd. for C$_{28}$H$_{38}$O: C, 86.10; H, 9.81. Found: C, 86.07;H, 10.18.

Example 18

Improved Procedure for Synthesis of RTMBE (2)

After RTMBE and 3a–3m were prepared as described above, the procedure for the preparation and purification of RTMBE was improved by employing a solution of 3,4,5-trimethoxybenzyl bromide in dimethylacetamide (DMAc), instead of the chloride in DMF; lowering the reaction temperature; and modifying the chromatographic purification. A solution of 28.7 g of the benzyl bromide in 450 mL of dry DMAc was added dropwise during 45 min to the lithium retinoxide solution (prepared at 10° C. from 31.5 g of retinol, 350 mL of dry benzene, and 68.7 mL of 1.6 M butyllithium in hexane). The reaction mixture was stirred at 20–25° C. during 1.5 h and then warmed at 35–40° C. during 1.5 h. The crude product, obtained as described from 3,4, 5-trimethoxybenzyl chloride, was dissolved in 75 mL of 95:5 hexane-ethyl acetate, and the solution was applied to a flash column prepared from 1700 g of silica gel 60 and 95:5 hexane-ethyl acetate. The column was developed with the same solvent (about 6 gallons) and eluted with 92.5:7.5 hexane-ethyl acetate (about 6 gallons). The elution was monitored by TLC. The forerun contained 2 and two minor components; subsequent eluent portions were combined and concentrated to a yellow syrup. Three portions of ethanol were added to and evaporated under reduced pressure from the syrup and the residue was dried to constant weight in vacuo: yield, 27.5 g (61%); HPLC, 99.1%; UV and $^1$H-NMR data as listed above.

Example 19

Analysis of Binding to CRBP and Other Properties

Binding affinities of the retinyl ethers for CRBP were determined by sucrose, density-gradient, sedimentation analysis as described before (Sani et al., 1980). Briefly, portions of rat testes cytosol (1 mg protein) were incubated with [$^3$H]retinol (50 pmol) in the presence or absence of a 150-fold molar excess of unlabeled retinol or the test retinoids. The preparations after dialysis were analyzed by 5–20% sucrose density gradient sedimentation. For measuring the competitive binding of the unlabeled retinoids, inhibition of [$^3$H]retinol binding to CRBP by unlabeled retinol is regarded as 100%. The mean and standard deviation calculated from the relative inhibitions obtained from multiple determinations were used as the relative binding affinities of the various retinyl ethers.

Because retinyl ethers lack the hydroxyl group of retinol, it might have been expected a priori that they would not bind to retinol-binding proteins; however, RME (Sani, 1993, Sani et al., 1996) and certain other retinyl ethers (Shealy et al., 1997) do indeed bind to cellular retinol-binding protein (CRBP). The group of retinyl benzyl ethers has now been evaluated for binding to CRBP. Binding to CRBP, as defined for Table I, at approximately 60% or higher was rated as strong; at 40–60%, as moderate; at 20–40%, as low. The results summarized in Table 2 show that some members of this group bind strongly to CRBP, whereas others do not bind effectively. Exclusive of the dichlorobenzyl ethers (3k,l), the structural requirements for strong or moderate binding of the benzyl ethers appear to be (1) two or more substituents and (2) at least one of these substituents at position 3 or 5 (2, 3a–c). The importance of the position of substitution is illustrated further by the two monomethoxybenzyl ethers; the 3-methoxy derivative (3f) has modest, but significant, binding affinity, whereas the 4-methoxy derivative (3e) does not. Structural patterns that are not conducive to CRBP binding are the absence of substituents (3d), the presence of only one substituent which is located at position 4 (3e,g), or the presence of substituents at positions 2 and 3 or 2 and 4 (3h–i). Surprisingly, the presence of a substituent adjacent to the ether oxygen (at the α-benzyl position, 3m) did not prevent binding, but rather resulted in strong binding.

Previously, it had been shown that RME also binds to serum retinol-binding protein (RBP); the inhibition of binding of tritiated retinol by a 150-fold molar excess of RME was the same as that (100%) of retinol (Sani et al., 1996). In the present studies, both RTMBE and RPE were shown to bind to RBP, the inhibition of [$^3$H] retinol-binding of both being 70% of that of retinol.

Earlier, several alkyl, alkenyl, or alkynyl retinyl ethers had been assayed for inhibition of TPA-induced ornithine decarboxylase (ODC) in mouse skin and for the suppression of DMBA-initiated and TPA-promoted mouse-skin papillomas (Shealy et al., 1997). In comparison with control groups, these retinyl ethers were ineffective. Only a few representatives of the benzyl ethers were selected for tests in these assays. RTMBE, the 3,4-dimethoxybenzyl ether (3a), and the 2,5-dimethoxybenzyl ether (3b) were not active in the ODC assay of Venna and Boutwell (1977) and Venna et al. (1978); the latter two benzyl ethers were also tested in the mouse-skin papilloma assay (Verma et al. 1979) and were ineffective in inhibiting papilloma formation. Because of these and the earlier results (Shealy et al., 1997), testing of retinyl benzyl ethers in the ODC and papilloma assays was discontinued.

As stated above, RME was reported to be demethylated to retinol in rat liver (Thompson and Pitt, 1963; Narindrasorasak et al., 1971; Narindrasorasak and Lakshmanan 1972). In addition, a study by Shih et al. (1991) showed that RME and the TMMP analogue of RME were converted, respectively, to retinol or its TMMP analogue by both constitutive and induced NADPH-requiring enzymes in rat liver microsomes. Because it was postulated, as stated above, that new retinyl ethers might not be converted by mircrosomal oxidases to retinol, RTMBE and 3a–i were tested in vitro in the same way. Conversion of these ethers to retinol was not detectable.

TABLE 2

Retinyl Benzyl Ethers Binding to CRBP

CRBP Assay

| Compound | No. of Assays | Percent Inhibition[a] of [$^3$H] Retinol Binding |
|---|---|---|
| 2 | 5 | 66 ± 12 |
| 3a | 5 | 62 ± 8 |
| 3b | 5 | 59 ± 13 |
| 3c | 5 | 65 ± 10 |
| 3d | 3 | 5 ± 5 |
| 3e | 3 | 7 ± 7 |
| 3f | 3 | 20 ± 5 |
| 3g | 3 | 0 |
| 3h | 3 | 0 |
| 3i | 3 | 5 ± 5 |
| 3j | 3 | 7 ± 6 |
| 3k | 3 | 0 |
| 3l | 3 | 40 ± 5 |
| 3m | 2 | 60 ± 0 |
| RME | 5 | 84[b] ± 4 |
| RPE | 3 | 60[b] ± 9 |

[a]Per cent inhibition of binding of tritiated retinol to CRBP by a 150-fold molar excess of the unlabelled test retinoid (Sani et al., 1980, 1996).
[b]Shealy et al., 1997

Example 20

Bioassay for Chemopreventive Activity Against MNU-Induced Mammary Cancer in Rats The methods employed in the preparation of diets, analyses of retinoid-diet specimens, and dietary treatment with retinoids of MNU-induced mammary carcinogenesis in Sprague-Dawley rats were described previously (Grubbs et al., 1995; Shealy et al., 1997). Briefly, diets were prepared by mixing each retinoid with Wayne meal or Teklad (4%) mash diet. For each kg of diet, the retinoid was dissolved in 12 g ethanol, 19 g trioctanoin, 0.05 mL Tenox 20, and 0.05 mL d,1-alpha tocopherol prior to incorporation into the feed using a Patterson-Kelly blender. Retinoid diet mixtures were stored at 4° C. Portions of each retinoid-diet mixture were analyzed for the added retinoid to ensure homogeneity. Female Sprague-Dawley rats received an i.v. injection of MNU (45 mg/kg body weight) at 50 days of age. Diet supplementation with retinoids was initiated three days after MNU. A group of rats receiving retinyl acetate (1 mmol/kg of diet) served as the positive control. The animals were palpated for mammary tumors 2x/week. At termination of the study, mammary tumors were processed for histological classification. Also, five rats/group had complete necropsies performed. The tissues were examined histologically for pathological lesions as additional toxicological evaluation. Extracts of the liver and mammary gland (5 rats/group) were analyzed by HPLC for retinyl palmitate and/or for the dosed retinoid. Statistical analyses of cancer incidence and latency were determined using logrank analysis, while differences in cancer multiplicity were determined employing the Armitage test.

RTMBE was evaluated for preventive activity against MNU-induced mammary cancer in rats. In this assay, described previously (Grubbs et al., 1995; Shealy el al., 1997), a retinoid dissolved in a solution (vehicle) consisting of ethanol and trioctanoin plus small amounts of Tenox 20 and α-tocopherol was mixed with feed, and the mixture was fed to rats after intravenous injection of MNU. The results of a 160-day study are summarized in Table 3 and FIG. 1. At doses of 1 and 2 millimoles of RTMBE per kilogram of feed, the average number of tumors per rat was reduced by 46% and 45%, respectively. In this experiment, retinyl acetate at 1 mmol/kg reduced the number of tumors by 30%. In a second, confirmatory experiment, RTMBE fed during 180 days at 2 mmol/kg of diet also reduced adenocarcinoma formation somewhat more effectively than retinyl acetate.

TABLE 3

RTMBE vs MNU-Induced Mammary Cancer in Rats[a] 160 Days

| Expt. No. 1. Treatment[b] | Adeno carcinomas Avg. No. Per Rat | % of Control Group A | Final Body Wt., Grams | Liver Levels, μg/g of Liver RTMBE | Retinyl Palmitate |
|---|---|---|---|---|---|
| Vehicle + MNU; Control Group A | 6.5 | NA[c] | 265 | NA | 249 ± 17 |
| Retinyl Acetate, 1 mmol | 4.5 | 70 | 240 | NA | 5390 ± 203 |
| RTMBE, 2 mmol | 3.5[d] | 54 | 246 | 25 ± 3 | 318 ± 25 |
| RTMBE, 1 mmol | 3.6[d] | 55 | 255 | 14 ± 1 | 297 ± 13 |
| RTMBE, 0.5 mmol | 6.5 | 100 | 256 | 7 ± 1 | 271 ± 11 |
| None, Wayne Diet only; Control Group B | 0 | | 260 | NA | 293 ± 11 |

[a]Female Sprague-Dawley rats (10/group) received one i.v. injection of MNU (45 mg/kg of body weight) at 50 days of age. Diet supplementation with retinoids was initiated at 52 days of age and was continued until the study was terminated 160 days after administration of MNU.
[b]Treatment with retinoids is stated in millimoles of retinoid per kilogram of diet (Wayne meal).
[c]NA = not applicable
[d]Significantly different, P < 0.05, from Control Group A (Armitage test).

The 2,5-dimethoxybenzyl (3b) and 4-methoxybenzyl (3e) ethers were tested in the same way in a 90-day study. The tumor data (average number of adenocarcinomas per rat) indicated that 3b and 3e were effective, the reductions in the number of tumors per rat being 26–52% and 37–49%, respectively, at dosing amounts of 1 and 2 mmol/kg of diet (Table 4). The 2,5-dimethybenzyl (3c) and the 2,3-dimethoxybenzyl (3h) ethers, together with RTMBE for comparison, were likewise assayed according to the same methodology. Prior to the beginning of this study, specimens of the retinoid-diet mixtures were placed under the conditions that were employed during the storage and feeding of RTMBE, 3c, and 3h. The specimens were extracted with butanol, and the extracts were analyzed by HPLC. The results showed that these retinoids were essentially unchanged under the conditions that existed in the animal rooms during the actual assays (Table 5). After 90 days of dosing of these three retinoids at 2, 1, and 0.5 mmol/kg of diet, the tumor data showed that 3c and 3h were not effective in reducing the number of tumors per rat, whereas RTMBE and retinyl acetate (at 1 mmol/kg) effected reductions of 64% and 66%, respectively (Table 4). Testing of 3c and 3h was discontinued, but the RTMBE study was continued until the duration of the study was 180 days (Table 6). The results were similar to those of Experiment 1 (Table 3). The averages of the number of tumors per rat were reduced by 32–35%; in addition, the averages of the tumor weights per rat was 56–70% lower than the average tumor burden of the control group. Therefore, in three long-term experiments of 160–180 days, RTMBE suppressed MNU-induced mammary cancer.

During an earlier 90-day study, RPE (at a dose level of two millimoles per kilogram of diet) reduced the average number of tumors per rat by 48%(Shealy et al., 1997).

Subsequently, RPE was evaluated in a long-term (180-day) study. The effectiveness of RPE after 90 days was confirmed; the average number of tumors per rat was reduced by 44% (Table 7). Afterward, the action of RPE in reducing tumor formation declined, the reduction in the average number of tumors per rat being 16% by the end of the long-term study.

TABLE 4

Short-Term Assay of Retinyl Benzyl Ethers vs. MNU-Induced Mammary Cancer in Rats[a]

| Expt. No. | Retinoid[b] | Treatment[c] | Tumors Avg. No. per Rat | % of Control Gp. |
|---|---|---|---|---|
| 2 | None | Vehicle ± MNU | 3.5 | |
|  | 3b | 2 mmol | 2.6 | 74 |
|  | 3b | 1 mmol | 1.7[d] | 48 |
|  | 3b | 0.5 mmol | 2.7 | 77 |
|  | 3e | 2 mmol | 1.8[d] | 51 |
|  | 3e | 1 mmol | 2.2 | 63 |
|  | 3e | 0.5 mmol | 2.5 | 71 |
|  | Retinyl Acetate | 1 mmol | 1.2[d] | 34 |
| 3 | None | Vehicle ± MNU | 1.93 | |
|  | RTMBE | 2 mmol | 0.7[d] | 36 |
|  | RTMBE | 1 mmol | 0.7[d] | 36 |
|  | RTMBE | 0.5 mmol | 1.5 | 78 |
|  | 3c | 2 mmol | 2.1 | 109 |
|  | 3c | 1 mmol | 3.3 | 171 |
|  | 3c | 0.5 mmol | 2.0 | 104 |
|  | 3h | 2 mmol | 2.8 | 145 |
|  | 3h | 1 mmol | 2.0 | 104 |
|  | 3h | 0.5 mmol | 2.2 | 114 |

[a]Female Sprague-Dawley rats (10/group) received one i.v. injection of MNU at 50 days of age.
[b]Diet supplementation with retinoids was initiated at 52 days of age and was continued until the studies of 3b, 3c, 3e, and 3h were terminated 90 days after administration of MNU. The RTMBE experiment was continued until 180 days after MNU administration (Table VI).
[c]Treatment with retinoids is stated in millimoles of retinoid per kilogram of Teklad diet.
[d]Significantly different, P < 0.05, from vehicle + MNU group (Armitage test).

TABLE 5

Analysis of Feed Samples for Stability of Retinyl Ethers[a] Assayed in the Tests Summarized in Table 4, Expt. 3

| Time of Analysis[b] | RTMBE | 3c | 3h |
|---|---|---|---|
| Immediately After Mixing | 99.8 | 103 | 95 |
| After 1 week of 4° C. | 101 | 96 | 99.7 |
| After 1 day in food cup[c] | 97 | 106 | 95 |
| After 2 days in food cup | 104 | 96 | 94 |
| After 3 days in food cup[d] | 97.5 | 102 | 97.9 |
| Vehicle + Retinoid (only) | 97 | 100 | 98.7 |

[a]The values in each column are % recoveries of the retinyl ether from mixtures of the ether with feed samples and are based on the actual amounts of the ether that were added.
[b]The samples that were analyzed were mixtures of vehicle, retinoid, and feed (prepared as described by Shealy et al., 1997).
[c]Food cups were placed in animal cages within the room that housed the rats; therefore, temperature (22° C.) and lighting were identical to those in use during the in vivo tests.
[d]During the actual feeding experiments with supplementation with retinoids, the retinoid-diet mixtures were in the animal cages ≦ 3 days.

TABLE 6

180-Day Study of RTMBE for Suppression of Mammary Carcinogensis.[a]

| Expt. 3 Treatment[b] | Adenocarcinomas Avg. No. Per Rat | % of Control Gp. | Final Body Wt., g | Tumor Wt. Per Rat, g | RTMBE In Mammary Gland, μg/g | Liver Levels μg/g of Liver RTMBE | Retinyl Palmitate |
|---|---|---|---|---|---|---|---|
| Vehicle + MNU, Control Gp. | 6.27 | | 274 | 17 | | | 665 |
| RTMBE, 2 mmol | 4.27[c] | 68 | 246 | 5.14 | 1770 | 33 | 1660 |
| RTMBE, 1 mmol | 4.20[c] | 67 | 252 | 7.57 | 577 | 11 | 1110 |
| RTMBE, 0.5 mmol | 4.07[c] | 65 | 259 | 7.0 | 256 | 6 | 1120 |

[a]Each group of female Sprague-Dawley rats (10/group) received one intravenous injection of MNU (45 mg/kg of body weight) at 50 days of age. The study of RTMBE that was begun as summarized in TABLE 4 was continued until Day 180 after injection of MNU.
[b]Diet supplementation with retinoids was initiated at 52 days of age and was continued until the study was terminated at 180 days after MNU. Treatment with retinoids is stated in millimoles of retinoid per kilogram of Teklad diet.
[c]By the Armitage test, the statistical difference was P < 0.08.

TABLE 7

RPE Vs. MNU-Induced Mammary Tumors In Rats 180-Day Study[a]

| No. of Rats | Treatment[c] | Avg No. Per Rat[b] | | % of Control Gp. | | Avg. Body Wt., G. | |
|---|---|---|---|---|---|---|---|
| | | Day 90 | Day 180 | Day 90 | Day 180 | Day 90 | Day 180 |
| | With MNU[d] | | | | | | |
| 30 | Vehicle | 2.3 | 6.4 | | | 218 | 262 |
| 30 | RPE, 2 mmol | 1.3[e] | 5.4 | 56 | 84 | 212 | 249 |
| 30 | RPE, 0.5 mmol | 1.7 | 6.2 | 74 | 97 | 219 | 258 |
| 30 | Retinyl OAc, 1 mmol | 1.1[e] | 3.1 | 48 | 49 | 211 | 226 |
| | Without MNU | | | | | | |
| 10 | Vehicle | | 0 | | | 234 | 276 |
| 10 | RPE, 2 mmol | | 0 | | | 222 | 259 |
| 10 | RPE, 0.5 mmol | | 0 | | | 233 | 280 |

[a]RPE was effective in a prior 90-day study (Shealy et al., 1997).
[b]Average number of palpable mammary tumors.
[c]Diet supplementation with retinoids was initiated at 52 days of age and was continued until the study was terminated 180 days after administration of MNU. Treatment with retinoids is stated in millimoles of retinoid per kilogram of diet (Wayne meal).
[d]Female Sprague-Dawley rats received one i.v. injection of MNU (50 mg/kg of body weight) at 50 days of age.
[e]Significantly different, $P < 0.05$, from vehicle group (Armitage test).

Example 21

Pharmacological and Toxicological Analysis

The jugular veins of groups of three Sprague-Dawley rats (200–250 g) were cannulated, and the rats were dosed intravenously via a tail vein with a retinyl ether (5 mg/kg). The vehicle was 6% ethanol, 1% Tween 80, and 6% Emulphor in 0.9% saline; the retinoid concentration in the dosing solution was 3.3 mg/mL. At thirteen selected times after dosing (2 min through 24 hr), blood samples were collected through the jugular catheter and centrifuged to obtain plasma. After collection of the final blood sample, selected tissues were collected, wrapped in foil, frozen on dry ice, and stored at $-20°$ C. in the dark.

To plasma samples (50–200 µl), ten volumes of acetonitrile were added, and the preparations were centrifuged. The supernatants were evaporated to dryness under nitrogen and reconstituted in the mobile phase (see below). Tissues were homogenized in four volumes of water at $0°$ C., and each homogenate was extracted with acetonitrile (50 mL/g tissue). From this point, handling of plasma and tissue samples was identical. Portions (25–50 µl) of the reconstituted samples were analyzed by reverse-phase HPLC. The chromatographic system was composed of a Beckman solvent delivery module 110B, analogue interface module 406, programable detector module 166, and autosampler 507. The column was a Hypersil ODS, 5-µ, 250×4.6 mm. Elution was accomplished with a solvent of methanol:0.2% acetic acid (93.5:6.5, v/v) with the final solution containing 0.02% triethylamine. The flow rate was 1 mL/min, with detection at 340 nm.

Toxicological evaluations involving measurement of body weights and observations of clinical signs characteristic of retinoid toxicity were accomplished as previously described (Lin et al., 1996).

Overt toxicity was not evident when RTMBE and four of its congeners were administered in the feed during the studies of these retinoids in the MNU-mammary cancer model in rats. RTMBE and two of its analogues, together with RME and RPE, were selected for estimation of their toxicities to mice when administered during 28–29 days by gavage in corn oil (Table 8). Mice were evaluated for changes in body weight and for signs of clinical retinoid toxicity (hypervitaminosis A) including alopecia, scaly skin, and limping. In the first experiment, these retinyl ethers were given at equimicromolar doses at three dose levels. The retinyl benzyl ethers (RTMBE, 3c, and 3e) were then tested at higher doses in a second experiment. The body-weight data indicate that RME was the only retinyl ether that was toxic (<40 mg/kg/day) at the highest of the selected doses. There was no evidence of toxicity at the highest doses of RTMBE, 3c, and 3e—249, 431, and 433 mg/kg/day, respectively. At the highest dose of 43 mg/kg/day, RPE did not produce signs of toxicity. These findings support the observations that RTMBE, 3c, and 3e were not toxic in the mammary carcinogenesis studies (above) and that, in a similar study reported previously (Shealy et al., 1997), RPE was not toxic as RME was (at 2 mmol/kg of diet).

TABLE 8

Toxicity of Some Retinyl Ethers in Mice[a]

| Retinyl Ether | Expt. No.[b] | Dose mg/kg/ day | Dose μmol/kg/ day | Mean Body Weights (g) Day 1 | Mean Body Weights (g) Termination Day[b] | Mean Body Weights (g) Gain | Difference In Wt. Gain From Control % | Toxic Dose mg/kg day |
|---|---|---|---|---|---|---|---|---|
| Control, Corn Oil | 1 | 0 | 0 | 22.8 | 26.0 | 3.2 | | |
| | 2 | 0 | 0 | 20.9 | 24.3 | 3.4 | | |
| RTMBE[c] | 1 | 15.5 | 33.3 | 21.8 | 25.5 | 3.7 | +15.6 | |
| 2 | 1 | 31.1 | 66.6 | 21.7 | 25.6 | 3.9 | +21.9 | |
| | 1 | 62.1 | 133.1 | 22.5 | 25.5 | 3.0 | −6.3 | |
| | 2 | 62.2 | 133.2 | 21.0 | 24.3 | 3.3 | −2.9 | |
| | 2 | 124.3 | 266.4 | 20.5 | 23.8 | 3.3 | −2.9 | |
| | 2 | 248.7 | 532.8 | 20.9 | 24.4 | 3.5 | +2.9 | >249 |
| RDMeBE-2,5[d] | 1 | 13.5 | 33.3 | 21.6 | 25.1 | 3.5 | +9.4 | |
| 3c | 1 | 26.9 | 66.6 | 21.4 | 25.2 | 3.8 | +18.8 | |
| | 1 | 53.9 | 133.1 | 22.1 | 26.5 | 4.4 | +37.5 | |
| | 2 | 107.8 | 266.4 | 20.9 | 24.6 | 3.7 | +8.8 | |
| | 2 | 215.6 | 532.8 | 20.6 | 24.6 | 4.0 | +17.6 | |
| | 2 | 431.2 | 1065.6 | 20.2 | 24.3 | 4.1 | +20.6 | >431 |
| RMoBE-4[c] | 1 | 13.5 | 33.3 | 22.3 | 25.8 | 3.5 | +9.4 | |
| 3e | 1 | 27.1 | 66.6 | 21.9 | 26.2 | 4.3 | +34.4 | |
| | 1 | 54.1 | 133.1 | 21.1 | 24.7 | 3.6 | +12.5 | |
| | 2 | 108.3 | 266.4 | 20.3 | 23.6 | 3.3 | −2.9 | |
| | 2 | 216.6 | 532.8 | 20.7 | 24.2 | 3.5 | +2.9 | |
| | 2 | 433.3 | 1065.6 | 20.6 | 25.0 | 4.4 | +29.4 | >433 |
| RME[e] | 1 | 10 | 33.3 | 22.4 | 26.3 | 3.9 | +21.9 | |
| | 1 | 20 | 66.6 | 21.8 | 25.8 | 4.0 | +25 | |
| | 1 | 40 | 133.1 | 22.0 | 23.8 | 1.8 | −43.8 | >20, <40 |
| RPE[e] | 1 | 10.8 | 33.3 | 22.5 | 26.4 | 3.9 | +21.9 | |
| | 1 | 21.6 | 66.6 | 21.7 | 24.9 | 3.2 | 0 | |
| | 1 | 43.2 | 133.1 | 20.5 | 24.1 | 3.6 | +12.5 | >43 |

[a]CD-1 mice were 6–8 weeks old at the beginning of the experiments. Retinoids were administered daily in corn oil by oral intubation.
[b]Experiment 1, Day 29. Experiment 2, Day 28.
[c]No evidence of clinical toxicity (alopecia, scaly skin, limping) in Expt. 2.
[d]No evidence of clinical toxicity except for scaly skin in 1/6 at 1065 μmol/kg/day.
[e]In the feed of Sprague-Dawley rats after 90 days: RME > 1 mmole/kg of diet, < 2 mmole/kg of diet; RPE > 2 mmole/kg of diet; (Shealy, et al.., 1997).

The concentrations of RTMBE in the serum, mammary gland, and liver of rats, as well as the levels of RP in the liver, were determined after administration of RTMBE by gavage during 14 days (Table 9). During the interval between 7 and 14 days, serum concentrations of RTMBE did not change significantly and liver levels increased by only 22%, but concentrations in the mammary gland increased by more than two-fold. After 14 days, the liver levels of RP were only slightly higher than the levels of the vehicle group. In order to investigate further the accumulation of retinyl benzyl ethers in mammary tissue, RTMBE, the 2,5-dimethoxybenzyl ether (3b), and the 4-methoxybenzyl (3e) ether were administered intravenously (via a tail vein) at 5 mg/kg to female Sprague-Dawley rats (3 with each retinoid). Acetonitrile extracts of plasma and mammary tissue were analyzed by HPLC. The ratios of mammary tissue-to-plasma concentrations of RTMBE, 3b, and 3e were 183±77, 38±20, and 41±14, respectively, after 24 hr. Although the latter retinyl ethers inhibited MNU-induced mammary carcinogenesis (Table 4), they were less effective than was RTMBE in 90-day assays.

TABLE 9

Tissue Concentrations Resulting from Gavage of Female Sprague-Dawley Rats with RTMBE.

| Treatment[a] | Retinyl Palmitate In Liver, μg/g | RTMBE, μg/g Serum μg/mL | RTMBE, μg/g Mammary Gland μg/g | RTMBE, μg/g Liver μg/g |
|---|---|---|---|---|
| RTMBE | | | | |
| 14 mg/day, 7 days | 63.3 ± 2.8 | 16.3 ± 2.5 | 83.3 ± 7.3 | 78.9 ± 7.5 |
| Vehicle, 7 days | 53.4 ± 2.3 | — | — | |
| RTMBE | | | | |
| 14 mg/day, 14 days | 73.6 ± 4.7 | 17.3 ± 2.2 | 178 ± 11.1 | 96.1 ± 11.1 |
| Vehicle, 14 days | 65.6 ± 1.8 | — | — | — |

[a]The dose of 14 mg/day by gavage is equivalent to a feeding dose of 2 mmol/kg of diet.

Example 22

Chemoprevention of Human Breast Cancer

In breast cancer patients, who are post-disease, post-surgery or who have a known family risk, RTMBE is administered as a chemopreventive or prophylactic measure. The RTMBE is administered in a pharmaceutical composition at a dosage of about 0.1 mg/kg to about 1000 mg/kg daily, preferably about 1 mg/kg to about 500 mg/kg daily or most preferred about 1 mg/kg/day to about 100 mg/kg/day. Alternatively, Tamoxifen or Raloxifene is also administered in conjunction with RTMBE. Dosages for Tamoxifen and Raloxifene is based on the standard doses routinely used for these drugs.

While the invention has been disclosed in this patent application by reference to the details of preferred embodiments of the invention, it is to be understood that the disclosure is intended in an illustrative rather than in a limiting sense, as it is contemplated that modifications will readily occur to those skilled in the art, within the spirit of the invention and the scope of the appended claims.

LIST OF REFERENCES

Aig, E. et al. (1987). *Synthetic Communications* 17:419–429.

Blaner, W. S. and Olson, J. A. (1994). *The Retinols: Biology, Chemistry and Medicine*, M. B. Sporn et al. (Eds.), Raven Press, New York, pp. 426 et seq.

Early Breast Cancer Trialists' Collaborative Group (1988). *N. Engl. J Med.* 319:1681–1692.

Early Breast Cancer Trialists' Collaborative Group (1992a). *The Lancet* 339:1–15.

Early Breast Cancer Trialists' Collaborative Group (1992b). *The Lancet* 339:71–85.

Grubbs, C. J. et al. (1 977). Inhibition of Mammary Cancer by Retinyl Methyl Ether. *Cancer Res.* 37:599–602.

Grubbs, C. J. et al. (1995). Chemoprevention of Chemically-Induced Mammary Carcinogenesis by Indole-3-carbinol. *Anticancer Res.* 15:709–716.

Hill, D. L. and Grubbs, C. J. (1982). *Anticancer Res.* 2:111–124.

Hill, D. L. and Grubbs, C. J. (1992). *Ann. Rev. Nutrition* 12:161–181

Lin, T. -H. et al. (1996). Murine Toxicology and Pharmacology of UAB-8, a Conformationally Constrained Analogy of Retinoic Acid. *Toxicology and Applied Pharmacology* 139:310–316.

Loeliger, P. et al. (1980). *Eur. J Med.-Chim. Therapeutica* 15:9–15.

Lotan, R. et al. (1980). Relationships Among Retinoid Structure, Inhibition of Growth, and Cellular Retinoic Acid-Binding Protein in Cultured S91 Melanoma Cells. *Cancer Res.* 40:1097–1102.

Mayer, H. etal. (1978). *Experientia* 34:1105–1109.

McPhillips, D. M. et al. (1988). The Disposition and Toxicology of Retinyl Methyl Ether in Rats Dosed Orally. *Drug, Metabolism and Disposition* 16:683–689.

Modani, K. et al. (1986). *Arch. Derinatol. Res.* 278:302–306.

Moon, R. C. and Itri, L. M. (1984). *The Retinoids*, Vol. 2, M. B. Sporn et al. (Eds.), Academic Press, New York, pp. 327–371.

Moon, R. C. et al. (1994). *The Retinoids*: Biology, Chemistry and Medicine, M. B. Sporn et al. (Eds.), Raven Press, New York, pp. 573–595.

Nagai, M. et al. (1994). *Chem. Pharm. Bull.* 42:1545–1547.

Narindrasorasak, S. et al. (1971). The Metabolism of Retinyl Methyl Ether in the Rat In Vivo. *Biochemical J.* 122:427–43 1.

Narindrasorasak, S. and Lakshmanan, M. R. (1972). Conversion of Retinyl Methyl Ether into Retinol in the Rat In Vitro. *Biochemistry* 11:380–384.

Robeson, C. D. el al. (1955). Chemistry of Vitamin A. XXIV. The Synthesis of Geometric Isomers of Vitamin A Via Methyl β-Methylglutaconate. *J. Am. Chem. Soc.* 77:4111–4119.

Rosenberg, M. et al. (1982). *J. Org. Chem.* 47:2130–2134.

Shih, T. W. et al. (1991). Conversion of Retinoid Ethers to Alcohols by Enzymatic Activity Present in Rat Liver Microsomes. *Drug Metabolism and Disposition* 19:336–339.

Sani, B. P. et al. (1980). Separation, purification, and properties of Retinoic Acid- and Retinol-Binding Proteins from a Transplantable Murine Colon Tumor. *Biochim. Biophys. Acta* 624:226–236.

Sani, B. P. (1993). Binding Affinities of Retinoids to Their Binding Proteins/Receptors and Their Biological Activities. In Retinoids. *Progress in Research and Clinical Applications*. Livera, M. A.; Packer, L. (Eds.), pp. 237–247. Marcel Dekker: New York.

Sani, B. P. et al. (1996). Retinyl Methyl Ether: Binding to Transport Proteins and Effect on Transcriptional Regulation. *Biochem. Biophys. Res. Comm.* 223:293–298.

Shantz, E. M. et al. (1943). Anhydro ("cyclized") Vitamin A. *J. Am. Chem. Soc.* 65:901–906.

Shealey, Y. F. (1989). Synthesis and Evaluation of Some New Retinoids for Cancer Chemoprevention. *Preventive Medicine* 18:624–645.

Shealey, Y. F. et al. (1996). Intramolecular Diels-Alder Reactions of the Retinoid Side Chain. *Tetrahedron* 42:405–424.

Shealy, Y. F. el al. (1997). Retinyl Ethers as Cancer Chemopreventive Agents. Suppression of Mammary Cancer. *Anti-Cancer Drug Design*, 12, 15–33.

Sporn, M. B. et al. (1976). *Federation Proceedings* 35:1332–1338.

Sporn, M. B. (1977). *Curr. Concepts Nutr.* 6 (*Nutr. Cancer*) :1 19–130.

Sporn, M. B. (1980). *Cacinogenesis*, Vol.5: Modifiers of Chemical Carcinogenesis, T. J. Slaga (Ed.), Raven Press, New York, 99–109.

Sporn, M. B. and Roberts, A. B. (1984). *The Retinoids*, Vol. 1, M. B. Sporn et al. (Eds.), Academic Press, New York, pp. 235–279.

Thompson, J. N. and Pitt, G. A. J. (1963). The Conversion of Retinyl Methyl Ether (Vitamin A Methyl Ether) to Retinol (Vitamin A Alcohol) In Vivo. *Biochimica et Biophysica Acta* 78:753–755.

Thompson, H. J. et al. (1978). Effect of Retinoids on N-methyl-N-nitrosourea (MNU)-Induced Mammary Cancer. *Federation Proceedings* 37:261.

Vaezi, M. F. et al. (1994). *J. Med. Chem.* 37:4499–4507.

Verma, A. K. and Boutwell, R. K. (1977). *Cancer Research* 37:2196–2201.

Verma, A. K. et al. (1978). Inhibition of 12-O-Tetradecanoylphorbol 13-acetate-Induced Ornithine Decarboxylase Activity in Mouse Epidermis by Vitamin A Analogs (Retinoids). *Cancer Research* 38:793–801.

Verma, A. K. el al. (1979). Correlation of the Inhibition by Retinoids of Tumor Promoter-Induced Mouse Epidermal Ornithine Decarboxylase Activity and of Skin Tumor Promotion. *Cancer Research* 39:319–425.

What is claimed is:
1. A compound having the general formula

 (I)

wherein R and R$^1$ are independently H, OH, halogen, C$_1$–C$_{10}$-alkyl, C$_1$–C$_{10}$-alkyl halide, C$_1$–C$_{10}$-alkoxy, phenoxy or an aryl group; n is 0 or 1; Y is an unsubstituted or substituted aryl; and X is a structure selected from the group consisting of (a)

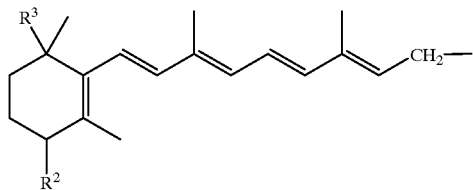

(b)

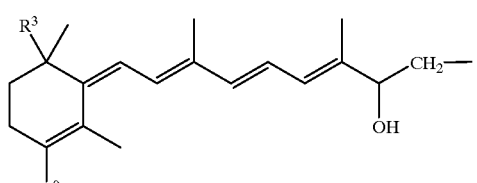

and (c)

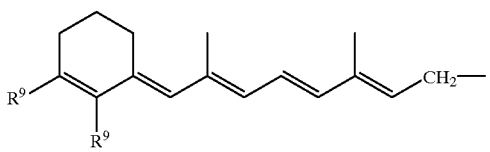

wherein R$^2$ is H, OH or =O, R$^3$ is CH$_3$ or CH$_2$OH, and R$^9$ is H, or C$_1$–C$_5$ alkyl, or a physiologically acceptable salt thereof, with the provisos that (1) when R and R$^1$ are both H, X is structure (a), R$^2$ is H, R$^3$ is CH$_3$ and n is 1, then Y is not trimethoxyphenyl or 4-ethynlphenyl; (2) when R$^2$ is H, R$^3$ is CH$_3$ X is structure (a) and n is 0, then Y is not 4-methoxyphenyl; (3) when R and R$^1$ are both H, X is structure (a), R$^2$ is H, R$^3$ is CH$_3$ and n is 1, then Y is not phenyl; and (4) when X is structure (a), n is 1 and Y is phenyl, then both R and R$^1$ are not phenyl.

2. The compound of claim 1 wherein X is structure (a).
3. The compound of claim 1 wherein X is structure (b).
4. The compound of claim 1 wherein X is structure (c).
5. The compound of claim 1 wherein Y is unsubstituted or substituted aryl.
6. The compound of claim 5 wherein the aryl is phenyl.
7. The compound of claim 5 wherein the aryl is naphthyl.

8. A method of inhibiting breast cancer in an individual which comprises administering to the individual an effective amount of a compound having the general formula

 (I)

wherein R and R$^1$ are independently H, OH, halogen, C$_1$–C$_{10}$-alkyl, C$_1$–C$_{10}$-alkyl halide, C$_1$–C$_{10}$-alkoxy, phenoxy or an aryl group; n is 0 or 1; Y is an unsubstituted or substituted aryl; and X is a stricture selected from the group consisting of (a)

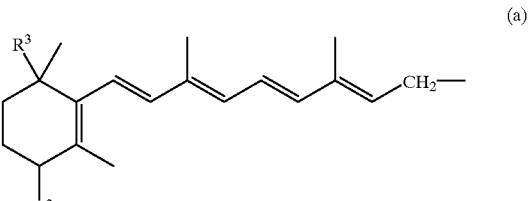

(b)

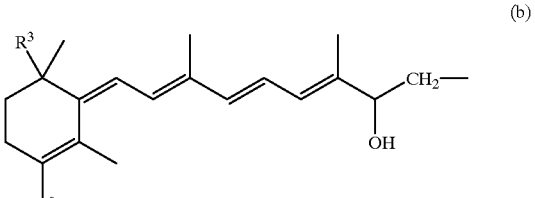

and (c)

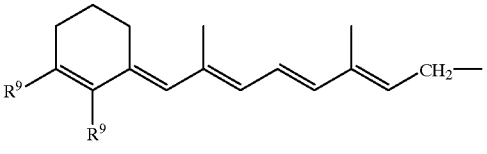

wherein R$^2$ is H, OH or =O, R$^3$ is CH$_3$ or CH$_2$OH, and R$^9$ is H, or C$_1$–C$_5$ alkyl, or a physiologically acceptable salt thereof.

9. The method of claim 8 wherein X is structure (a).
10. The method of claim 8 wherein X is structure (b).
11. The method of claim 8 wherein X is structure (c).
12. The method of claim 8 wherein Y is unsubstituted or substituted aryl.
13. The method of claim 12 wherein the aryl is phenyl.
14. The method of claim 12 wherein the aryl is naphthyl.
15. The method of claim 8 wherein a second antineoplastic agent is further administered to said individual.
16. The method of claim 8 wherein said effective amount is in the range from about 0.1 mg/kg/day to about 1,000 mg/kg/day.

* * * * *